US009062013B2

(12) United States Patent
Harvey et al.

(10) Patent No.: US 9,062,013 B2
(45) Date of Patent: Jun. 23, 2015

(54) POSITIVE ALLOSTERIC MODULATORS OF THE α7 NICOTINIC ACETYLCHOLINE RECEPTOR AND USES THEREOF

(75) Inventors: Andrew Harvey, Goodwood (AU); Audrey Fluck, Dangolsheim (FR); Bruno Giethlen, Altorf (FR); Dharam Paul, Flinders Park (AU); Laurent Schaeffer, Durrenentzen (FR)

(73) Assignee: Bionomics Limited, Thebarton (AU)

( * ) Notice: Subject to any disclaimer, the term of this patent is extended or adjusted under 35 U.S.C. 154(b) by 0 days.

(21) Appl. No.: 13/983,476

(22) PCT Filed: Feb. 2, 2012

(86) PCT No.: PCT/AU2012/000084
§ 371 (c)(1),
(2), (4) Date: Oct. 14, 2013

(87) PCT Pub. No.: WO2012/103583
PCT Pub. Date: Aug. 9, 2012

(65) Prior Publication Data
US 2014/0031395 A1  Jan. 30, 2014

(30) Foreign Application Priority Data
Feb. 2, 2011 (AU) .................. 2011900319

(51) Int. Cl.
*C07D 213/75* (2006.01)
*C07D 231/40* (2006.01)
*C07D 277/46* (2006.01)
*C07C 311/46* (2006.01)
*C07C 233/60* (2006.01)
*A61K 31/44* (2006.01)
*A61K 31/167* (2006.01)
*A61K 31/36* (2006.01)
*A61K 31/63* (2006.01)
*C07C 233/59* (2006.01)
*C07C 311/16* (2006.01)
*C07D 317/46* (2006.01)
*C07D 275/06* (2006.01)
*C07D 209/46* (2006.01)

(52) U.S. Cl.
CPC ............ *C07D 277/46* (2013.01); *C07C 233/59* (2013.01); *C07C 233/60* (2013.01); *C07C 311/16* (2013.01); *C07C 2101/02* (2013.01); *C07C 2102/50* (2013.01); *C07D 213/75* (2013.01); *C07D 231/40* (2013.01); *C07D 317/46* (2013.01); *C07C 311/46* (2013.01); *C07D 275/06* (2013.01); *C07D 209/46* (2013.01)

(58) Field of Classification Search
None
See application file for complete search history.

(56) References Cited

U.S. PATENT DOCUMENTS 5,286,736 A    2/1994  Soyka et al.
2009/0163545 A1*  6/2009  Goldfarb .................... 514/312

FOREIGN PATENT DOCUMENTS

WO    0055146       6/2001
WO    03082190      10/2003
WO    2010144959    12/2010
WO    2013020622    2/2013

OTHER PUBLICATIONS

Goldfarb et al, Chemical Abstract Service, Database Accession No. 151:92850 of US 2009/0163545 (Jun. 2009).*
Ahmad, Saleem, et al., "Arylcyclopropanecarboxyl Guanidines as Novel, Potent, and Selective Inhibitors of the Sodium Hydrogen Exchanger Isoform-1", J. Med. Chem., vol. 44, pp. 3302-3310, Aug. 30, 2001.
Banwell, Martin G., et al., "Synthesis, X-ray Crystal Structure, and Antimitotic Properties of 6-Chloro-2-methoxy-5-(2',3',4'-trimel hoxyphenyl)cyclohepta-2,4,6-trien-1-one, a Bicyclic Analogue of Colchicine", J. Org. Chem., vol. 53, No. 21, pp. 4945-3952, Oct. 1, 1988.
Dolbier, William R., Jr., et al., "Trimethylsilyl fluorosulfonyldifluoroacetate (TFDA): a new, highly efficient difluorocarbene reagent", J. Fluorine Chem., vol. 125, pp. 459-469, Dec. 2, 2003.
Drygala, Peter F., et al., "A Convenient Synthesis of 2-Hydroxybenzenesulfonamide", Synthetic Communications, vol. 24, No. 5, pp. 671-675, 1994.
Edwards, Michael G., et al., "gem-Dimethylcyclopropanation Using Triisopropylsulfoxonium Tetrafluoroborate: Scope and Limitations", Synthesis, 2008, No. 20, pp. 3279-3288, Sep. 25, 2008.
Graf, Roderich, "Uber das Sulfamidsaurechlorid", Chemische Berichte, vol. 92, pp. 509-513, 1959.
Lin, Shaw-Tao, et al., "Preparation of arylspiro[2,4]hept-5-enes from aryldibromocyclopropanes via diallylation and metathesis reaction", J. Chem. Res., Sep. 2003, pp. 591-592.
Nishimura, J., et al., "A novel synthesis of methylcyclopropanes", Tetrahedron, vol. 25, pp. 2647-2659, 1969.
Perollier, et al., "A convenient access to N,N-distributed amides derived from (1r,3s)-(–)-2,2-dimethyl-3-formylcyclopropane-1-carboxylic acid", Bulletin de la Societe Chimique de France, 1997, vol. 134, No. 5, pp. 517-523.
Farkas, Jiri, et al., "Relation between chemical structure and insecticidal activity in pyrethyroid compounds. II. Analogs of chrysanthemic acid containing an aryl group", Chemicke Listy pro Vedu a Prumysl, 1958, vol. 52, pp. 695-706.
Results of Substructure Search, Aurora Screening Library, Aurora Fine Chemicals, LLC, http://online.aurorafinechemicals.com/structure-search.asp, (2015).

* cited by examiner

*Primary Examiner* — Zinna Northington Davis
(74) *Attorney, Agent, or Firm* — Honigman Miller Schwartz & Cohn LLP; Thomas A. Wootton, Esq.; Jonathan P. O'Brien

(57) ABSTRACT

The present invention relates to compounds useful in the positive modulation of the alpha 7 nicotinic acetylcholine receptor (α7nAChR). The invention also relates to the use of these compounds in the treatment or prevention of a broad range of diseases in which the positive modulation of α7nAChR is advantageous, including neurodegenerative and neuropsychiatric diseases and also inflammatory diseases.

18 Claims, No Drawings

POSITIVE ALLOSTERIC MODULATORS OF THE α7 NICOTINIC ACETYLCHOLINE RECEPTOR AND USES THEREOF

CONTINUING DATA

This application is a 371 of PCT/AU2012/000084 filed Feb. 2, 2012.

FIELD OF THE INVENTION

The present invention relates to chemical compounds useful in the positive modulation of the alpha 7 nicotinic acetylcholine receptor (α7nAChR). The invention also relates to the use of these compounds in the treatment or prevention of a broad range of diseases in which the positive modulation of α7nAChR is advantageous, including neurodegenerative and neuropsychiatric diseases and also inflammatory diseases.

BACKGROUND

The alpha 7 nicotinic acetylcholine receptors (α7nAChRs) are rapidly desensitizing ligand-gated ion channels that are abundantly expressed in the cerebral cortex and the hippocampus, a limbic structure intimately linked to attention processing and memory formation. α7nAChRs modulate neurotransmitter release and are responsible for direct fast excitatory neurotransmission. At the cellular level, activation of α7nAChRs can regulate interneuron excitability, modulate the release of excitatory and inhibitory neurotransmitters, and contribute to neuroprotective effects.

Several lines of evidence indicate that attention and cognitive impairment, which are characteristic of neurological and psychiatric disorders such as Alzheimer's disease (AD), schizophrenia, Parkinson's Disease (PD), multiple sclerosis, attention deficit hyperactivity disorder (ADHD), mild cognitive impairment (MCI), age associated memory impairment (AAMI), may involve degeneration or hypo-function of cholinergic input. Moreover, genetic linkage has identified α7AChRs as a predisposing factor related to sensory gating deficits. Thus, targeting the α7nAChRs represents a therapeutic strategy for ameliorating cognitive deficits associated with neurodegenerative and neuropsychiatric diseases.

A number of reports also suggest that α7nAChRs mediate protection against neurotoxicity induced by amyloid beta and excitotoxic insults. Peripherally, α7-nAChRs are expressed in macrophages and their stimulation is essential for inhibiting the release of proinflammatory cytokines (e.g. TNF-a, IL-1) via the cholinergic anti-inflammatory pathway which is triggered in response to signals from the vagus nerve. Thus, the clinical use of agonists of the α7nAChRs could also represent a strategy against inflammatory diseases.

Selective positive allosteric modulation (PAM) of the α7nAChR is a recent therapeutic approach for treating these disease states. A key advantage of this approach is that modulation only occurs in the presence of endogenous agonist thereby preserving the temporal and spatial integrity of neurotransmission. At least two different profiles of PAMs have been described thus far for α7nAChRs: Type I modulators that predominately affect the apparent peak current and agonist sensitivity, and Type II modulators that also cause a modification of the desensitization profile of agonist response. Several potent PAMs have been described (for example, 5-hydroxyindole, NS-1738) that increase acetylcholine sensitivity with only marginal effects on the desensitization kinetics of the α7nAChR channel. Others such as PNU-120596, show profound effects on receptor desensitization in addition to enhanced sensitivity to acetylcholine and increased current amplitude.

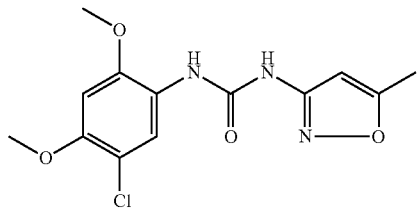

PNU-120596

The present invention seeks to address some of the shortcomings of the prior art therapeutics and is directed to a new class of compounds which are thought to exhibit positive modulation of α7nAChR.

SUMMARY OF THE INVENTION

In one aspect the invention provides compounds of formula (I) or salts thereof:

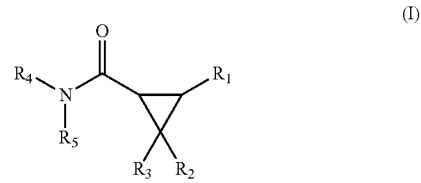

(I)

wherein
  $R_1$ is selected from optionally substituted aryl, optionally substituted heteroaryl (excluding optionally substituted porphyrins), or optionally substituted heterocyclyl;
  $R_2$ is selected from $C_1$-$C_4$ alkyl, $C_3$-$C_5$ alkenyl, F, Br, Cl, CN, or $C_1$-$C_4$ haloalkyl;
  $R_3$ is selected from hydrogen, $C_1$-$C_4$ alkyl, $C_3$-$C_5$ alkenyl, F, Br, Cl, CN, or $C_1$-$C_4$ haloalkyl; or
  $R_2$ and $R_3$ together form $C_{4-9}$ cycloalkyl or $C_{4-9}$ cycloalkenyl;
  $R_4$ is selected from optionally substituted heteroaryl, optionally substituted heterocyclyl, or optionally substituted aryl;
  $R_5$ is selected from hydrogen or optionally substituted alkyl;
  wherein when both $R_2$ and $R_3$ are $C_1$, $R_4$ is an optionally substituted heteroaryl or optionally substituted heterocyclyl,
  provided that the following compounds are excluded:

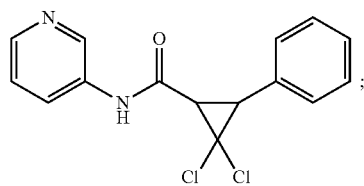

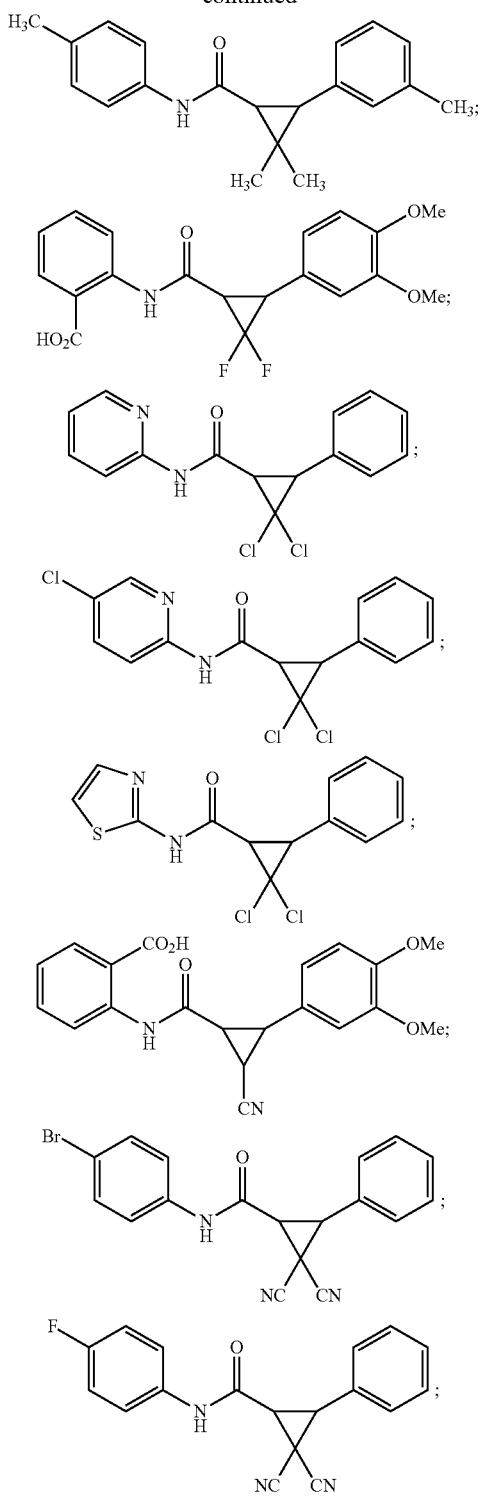

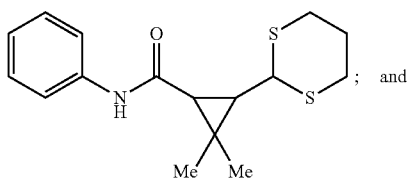

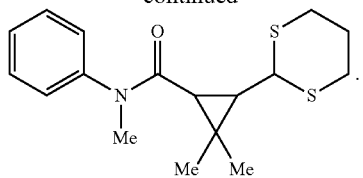

In an embodiment $R_1$ is an optionally substituted aryl group and more preferably an optionally substituted phenyl group.

Accordingly, in a further aspect the invention provides compounds of formula (Ia) or salts thereof:

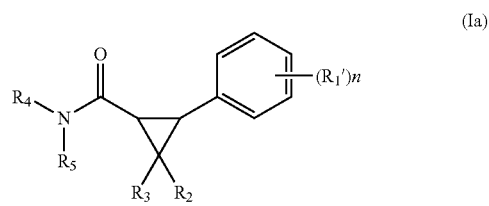

(Ia)

wherein each $R_1'$ is independently selected from the group consisting of cyano, halo, nitro, optionally substituted lower alkyl, optionally substituted aryl, optionally substituted aryloxy, optionally substituted arylalkyl, optionally substituted heteroaryl, optionally substituted heterocyclyl, optionally substituted $C_{3-7}$ cycloalkyl, —OR, —C(O)R, —C(O)OR, —OC(O)R (where R is selected from hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl), —C(O)NR'R", —NRC(O)R", —S(O)$_2$—NR'R" and —NR'R" (where R' and R" are independently selected from hydrogen or lower alkyl), —S(O)R''' (where R''' is lower alkyl, or cycloalkyl), —S(O)$_2$R''' (where R''' is lower alkyl, cycloalkyl or OH), or any two adjacent $R_1'$ together form heterocyclyl or heteroaryl;

n is 0 or an integer from 1 to 5;

$R_2$ is selected from $C_1$-$C_4$ alkyl, $C_3$-$C_5$ alkenyl, F, Br, Cl, CN, or $C_1$-$C_4$ haloalkyl;

$R_3$ is selected from hydrogen, $C_1$-$C_4$ alkyl, $C_3$-$C_5$ alkenyl, F, Br, Cl, CN, or $C_1$-$C_4$ haloalkyl; or $R_2$ and $R_3$ together form $C_{4-9}$ cycloalkyl or $C_{4-9}$ cycloalkenyl;

$R_4$ is selected from optionally substituted heteroaryl, optionally substituted heterocyclyl, or optionally substituted aryl;

$R_5$ is selected from hydrogen or optionally substituted alkyl;

wherein when both $R_2$ and $R_3$ are $C_1$, $R_4$ is an optionally substituted heteroaryl or optionally substituted heterocyclyl, provided that the following compounds are excluded:

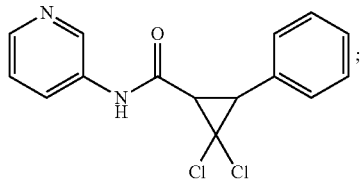

-continued

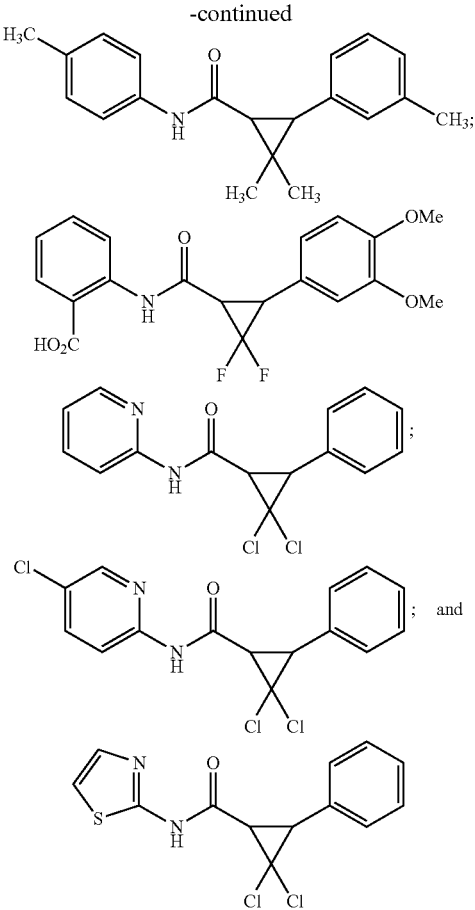

In another embodiment $R_3$ and $R_2$ together form a $C_4$-$C_9$ cycloalkyl.

Accordingly, in a further aspect the invention provides compounds of formula (II) or salts thereof:

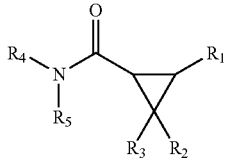

(II)

wherein
$R_1$ is selected from optionally substituted aryl, optionally substituted heteroaryl or optionally substituted heterocyclyl;
$R_2$ and $R_3$ together form $C_{4-9}$ cycloalkyl;
$R_4$ is selected from optionally substituted heteroaryl, optionally substituted heterocyclyl, or optionally substituted aryl; and
$R_5$ is selected from hydrogen or optionally substituted alkyl.

In a further aspect the invention provides a method for the treatment or prevention of cognitive deficits associated with neurodegeneration or neuropsychiatric diseases, said method including the step of administering a compound of formula (I), (Ia) or (II), or a pharmaceutically acceptable salt thereof, or a composition comprising a compound of formula (I), (Ia) or (II), or a pharmaceutically acceptable salt thereof.

In still a further aspect the invention provides a method for the treatment or prevention of inflammatory diseases, said method including the step of administering a compound of formula (I), (Ia) or (II), or a pharmaceutically acceptable salt thereof, or a composition comprising a compound of formula (I), (Ia) or (II), or a pharmaceutically acceptable salt thereof.

In another aspect the invention provides the use of a compound of formula (I), (Ia) or (II), or a salt thereof in the manufacture of a medicament for the treatment or prevention of cognitive deficits associated with neurodegeneration or neuropsychiatric diseases.

In another aspect the invention provides the use of a compound of formula (I), (Ia) or (II), or a salt thereof in the manufacture of a medicament for the treatment or prevention of inflammatory diseases.

In another aspect of the invention there is provided a method of positively modulating α7nAChRs in a cell by contacting the cell with a compound of formula (I), (Ia) or (II), or a pharmaceutically acceptable salt thereof, to said cell.

In a further aspect of the invention there is provided a pharmaceutical composition for use as a neuroprotective agent, the composition comprising an effective amount of a compound of formula (I), (Ia) or (II), or a pharmaceutically acceptable salt thereof and optionally a carrier or diluent.

In still a further aspect of the invention there is provided a pharmaceutical composition for use as an anti-inflammatory agent, the composition comprising an effective amount of a compound of formula (I), (Ia) or (II), or a pharmaceutically acceptable salt thereof and optionally a carrier or diluent.

In another aspect of the invention there is provided a process for the preparation of compounds of formula (I), (Ia) or (II), or salts thereof.

DETAILED DESCRIPTION OF THE INVENTION

The term "alkyl" as used alone or in combination herein refers to a straight or branched chain saturated hydrocarbon group. The term "$C_{1-12}$ alkyl" refers to such a group containing from one to twelve carbon atoms and "lower alkyl" refers to $C_{1-6}$ alkyl groups containing from one to six carbon atoms, such as methyl ("Me"), ethyl ("Et"), n-propyl, isopropyl, n-butyl, isobutyl, sec-butyl, tert-butyl and the like.

The term "cycloalkyl" refers to non-aromatic, saturated non-aromatic carbocycles. The term "$C_{4-9}$ cycloalkyl", for instance, refers to such a group having from 4 to 9 carbon atoms. Examples include cyclobutyl, cyclopentyl and cyclohexyl.

The term "alkenyl" refers to a straight or branched hydrocarbon containing one or more double bonds, preferably one or two double bonds. The term "$C_{2-12}$ alkenyl", for instance, refers to such a group containing from two to twelve carbon atoms. Examples of alkenyl include allyl, 1-methylvinyl, butenyl, iso-butenyl, 1,3-butadienyl, 3-methyl-2-butenyl, 1,3-butadienyl, 1,4-pentadienyl, 1-pentenyl, 1-hexenyl, 3-hexenyl, 1,3-hexadienyl, 1,4-hexadienyl and 1,3,5-hexatrienyl.

The term "cycloalkenyl" refers to cyclic alkenyl groups having a single cyclic ring or multiple condensed rings, and at least one point of internal unsaturation, preferably incorporating 4 to 11 carbon atoms. Examples of suitable cycloalkenyl groups include, for instance, cyclobut-2-enyl, cyclopent-3-enyl, cyclohex-4-enyl, cyclooct-3-enyl, indenyl and the like.

The term "alkynyl" refers to a straight or branched hydrocarbon containing one or more triple bonds, preferably one or two triple bonds. The term "$C_{2-12}$ alkynyl", for instance, refers to such a group containing from two to twelve carbon atoms. Examples include 2-propynyl and 2- or 3-butynyl.

The term "alkoxy" as used alone or in combination refers to a straight or branched chain alkyl group covalently bound via an oxygen linkage (—O—) and the terms "$C_{1-6}$ alkoxy" and "lower alkoxy" refer to such groups containing from one to six carbon atoms, such as methoxy, ethoxy, propoxy, isopropoxy, butoxy, t-butoxy and the like.

The term "aryl" refers to carbocyclic (non-heterocyclic) aromatic rings or ring systems. The aromatic rings may be mono- or bi-cyclic ring systems. The aromatic rings or ring systems are generally composed of 5 to 10 carbon atoms. Examples of suitable aryl groups include but are not limited to phenyl, biphenyl, naphthyl, tetrahydronaphthyl, and the like. Preferred aryl groups include phenyl, naphthyl, indenyl, azulenyl, fluorenyl or anthracenyl.

The term "heteroaryl" refers to a monovalent aromatic carbocyclic group, preferably of from 2 to 10 carbon atoms and 1 to 4 heteroatoms selected from oxygen, nitrogen and sulfur within the ring. Preferably the heteroatom is nitrogen. Such heteroaryl groups can have a single ring (e.g., pyridyl, pyrrolyl or furyl) or multiple condensed rings (e.g., indolizinyl or benzothienyl).

The term "heterocyclyl" refers to a monovalent saturated or unsaturated group having a single ring or multiple condensed rings, preferably from 1 to 8 carbon atoms and from 1 to 4 hetero atoms selected from nitrogen, sulfur, oxygen, selenium or phosphorous within the ring.

Examples of 5-membered monocyclic heterocyclyl and heteroaryl groups include furyl, thienyl, pyrrolyl, H-pyrrolyl, pyrrolinyl, pyrrolidinyl, oxazolyl, oxadiazolyl, (including 1,2,3 and 1,2,4 oxadiazolyls) thiazolyl, isoxazolyl, furazanyl, isothiazolyl, pyrazolyl, pyrazolinyl, pyrazolidinyl, imidazolyl, imidazolinyl, triazolyl (including 1,2,3 and 1,3,4 triazolyls), tetrazolyl, thiadiazolyl (including 1,2,3 and 1,3,4 thiadiazolyls).

Examples of 6-membered monocyclic heterocyclyl and heteroaryl groups include pyridyl, pyrimidinyl, pyridazinyl, pyranyl, pyrazinyl, piperidinyl, 1,4-dioxanyl, morpholinyl, 1,4-dithianyl, thiomorpholinyl, piperazinyl, 1,3,5-trithianyl and triazinyl.

Examples of 8, 9 and 10-membered bicyclic heterocyclyl and heteroaryl groups include 1H thieno[2,3-c]pyrazolyl, thieno[2,3-b]furyl, indolyl, isoindolyl, benzofuranyl, benzothienyl, benzoxazolyl, benzothiazolyl, benzisoxazolyl, benzisothiazolyl, benzimidazolyl, indazolyl, isoquinolinyl, quinolinyl, quinoxalinyl, uridinyl, purinyl, cinnolinyl, phthalazinyl, quinazolinyl, quinoxalinyl, benzotriazinyl, naphthyridinyl, pteridinyl and the like.

The term "arylalkyl" refers to carbocyclic aromatic rings or ring systems as previously described and substituted by an alkyl group, also as previously described. Unless otherwise indicated the aryl substituent is attached by the alkyl part of the substituent. Likewise the terms "aryl $C_{1-12}$ alkyl", "aryl $C_{2-12}$ alkenyl" and "aryl $C_{2-12}$ alkynyl" refer to carbocyclic aromatic rings or ring systems as previously described and substituted by a $C_{1-12}$ alkyl, $C_{2-12}$ alkenyl or $C_{2-12}$ alkynyl group, as previously described.

The terms "halo" and "halogen" refers to fluoro, chloro, bromo and iodo groups.

The term "halo alkyl" group has one or more of the hydrogen atoms on an alkyl group replaced with halogens. A notable example is —$CF_3$.

The term "aryloxy" refers to an aryl group as earlier described linked to the parent structure via an oxygen linkage (—O—). A notable example is phenoxy. Similarly the term "heteroaryloxy" refers to a heteroaryl group as earlier described linked to the parent structure via an oxygen group. A notable example is a 4, 6 or 7-benzo[b]furanyloxy group.

The term "optionally substituted" means that a group may include one or more substituents. One or more hydrogen atoms on the group may be replaced by substituent groups independently selected from halogens (for example halo alkyl such as —CF), $C_{1-6}$ alkyl, $C_{2-6}$ alkenyl, $C_{2-6}$ alkynyl, —$(CH_2)_pC_{3-7}$ cycloalkyl, —$(CH_2)_pC_{4-7}$ cycloalkenyl, —$(CH_2)_p$ aryl, —$(CH_2)_p$ heterocyclyl, —$(CH_2)_p$ heteroaryl, —$C_6H_4S(O)_qC_{1-6}$ alkyl, —C(Ph)$_3$, —CN, —OR, —O—$(CH_2)_{1-6}$—R, —O—$(CH_2)_{1-6}$—OR, —OC(O)R, —C(O)R, —C(O)OR, —OC(O)NR'R", —NR'R", —NRC(O)R', —NRC(O)NR'R", —NRC(S)NR'R", —NRS(O)$_2$R', —NRC(O)OR', —C(NR)NR'R", —C(=NOR')R, —C(=NOH)NR'R", —C(O)NR'R", —C(=NCN)—NR'R", —C(=NR)NR'R", —C(=NR')SR", —NR'C(=NCN)SR", —CONRSO$_2$R, —C(S)NR'R", —S(O)$_q$R, —SO$_2$NR'R", —SO$_2$NRC(O)R', —OS(O)$_2$R, —PO(OR)$_2$ and —NO$_2$;

where p is 0-6, q is 0-2 and each R, R' and R" is independently selected from H, $C_{1-6}$ alkyl, $C_{2-6}$ alkenyl, $C_{2-6}$ alkynyl, $C_{3-7}$ cycloalkyl, $C_{4-7}$ cycloalkenyl, aryl, heterocyclyl, heteroaryl, $C_{1-6}$ alkylaryl, $C_{1-6}$ alkylheteroaryl, and $C_{1-6}$ alkylheterocyclyl, wherein the alkyl, alkenyl, alkynyl, cycloalkyl, cycloalkenyl, aryl, heterocyclyl, heteroaryl, $C_{1-6}$ alkylaryl, $C_{1-6}$ alkylheteroaryl, or $C_{1-6}$ alkylheterocyclyl, may be optionally substituted with one to six of same or different groups selected from halogen, hydroxy, lower alkyl, lower alkoxy, —CO$_2$H, CF$_3$, CN, phenyl, NH$_2$ and —NO$_2$; or when R' and R" are attached to the same nitrogen atom, they may, together with the atom to which they are attached, form a 5 to 7 membered nitrogen containing heterocyclic ring.

A list of preferred optional substituents includes: halogen (in particular, Cl, Br or F), $C_{1-6}$ alkyl, $C_{1-6}$ alkoxy, $C_{2-6}$ alkenyl, $C_{2-6}$ alkynyl, $C_{1-6}$ haloalkyl (in particular —CF$_3$), $C_{1-6}$ haloalkoxy (such as —OCF$_3$), —OH, phenyl, benzyl, phenoxy, benzyloxy, benzoyl, —NH$_2$, —NHC$_{1-4}$ alkyl, —N(C$_{1-4}$ alkyl)$_2$, —CN, —NO$_2$, mercapto, —S(O)$_2$NH$_2$, —S(O)$_2$NHC$_{1-4}$ alkyl, —S(O)$_2$N(C$_{1-4}$ alkyl)$_2$, $C_{1-6}$ alkylcarbonyl, $C_{1-6}$ alkoxycarbonyl, CO$_2$H, —S(O)R''' (where R''' is lower alkyl or cycloalkyl) and —S(O)$_2$R''' (where R''' is lower alkyl, cycloalkyl or OH).

Unless otherwise defined and only in respect of the ring atoms of non-aromatic carbocyclic or heterocyclic compounds, the ring atoms of such compounds may also be optionally substituted with one or two =O groups, instead of or in addition to the above described optional substituents.

When the optional substituent is or contains an alkyl, alkenyl, alkynyl, cycloalkyl, aryl, heteroaryl or heterocyclyl group, the group may itself be optionally substituted with one to six of the same or different substituents selected from halogen, $C_{1-6}$ alkyl, $C_{1-6}$ alkoxy, $C_{2-6}$ alkenyl, $C_{2-6}$ alkynyl, $C_{1-6}$ haloalkyl (in particular —CF$_3$), $C_{1-6}$ haloalkoxy (such as —OCF$_3$), —OH, phenyl, benzyl, phenoxy, benzyloxy, benzoyl, —NH$_2$, —NHC$_{1-4}$ alkyl, —N(C$_{1-4}$ alkyl)$_2$, —CN, —NO$_2$, mercapto, —S(O)$_2$NH$_2$, —S(O)$_2$NHC$_{1-4}$ alkyl, —S(O)$_2$N(C$_{1-4}$ alkyl)$_2$, $C_{1-6}$ alkylcarbonyl, $C_{1-6}$ alkoxycarbonyl, CO$_2$H, —S(O)R''' (where R''' is lower alkyl or cycloalkyl) and —S(O)$_2$R''' (where R''' is lower alkyl, cycloalkyl or OH).

In an embodiment R$_2$ is selected from $C_1$-$C_4$ alkyl, $C_3$-$C_5$ alkenyl, $C_1$-$C_4$ haloalkyl, F, Cl or Br, and R$_3$ is selected from hydrogen, $C_1$-$C_4$ alkyl, $C_3$-$C_5$ alkenyl, $C_1$-$C_4$ haloalkyl, or Br.

Accordingly, in another aspect the invention provides compounds of formula (Ib), or salts thereof:

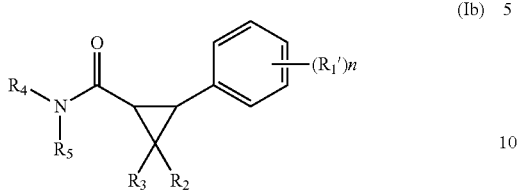

(Ib)

wherein
each $R_1'$ is independently selected from the group consisting of cyano, halo, nitro, optionally substituted lower alkyl, optionally substituted aryl, optionally substituted aryloxy, optionally substituted arylalkyl, optionally substituted heteroaryl, optionally substituted heterocyclyl, optionally substituted $C_{3-7}$ cycloalkyl, —OR, —C(O)R, —C(O)OR, —OC(O)R (where R is selected from hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl), —C(O)NR'R", —NR'C(O)R", —S(O)$_2$—NR'R" and —NR'R" (where R' and R" are independently selected from hydrogen or lower alkyl), —S(O)R''' (where R''' is lower alkyl, or cycloalkyl), —S(O)$_2$R''' (where R''' is lower alkyl, cycloalkyl or OH), or any two adjacent $R_1'$ together form heterocyclyl or heteroaryl;

n is 0 or an integer from 1 to 5;

$R_2$ is selected from $C_1$-$C_4$ alkyl, $C_3$-$C_5$ alkenyl, $C_1$-$C_4$ haloalkyl, F, Cl or Br;

$R_3$ is selected from hydrogen, $C_1$-$C_4$ alkyl, $C_3$-$C_5$ alkenyl, $C_1$-$C_4$ haloalkyl, or Br; or $R_2$ and $R_3$ together form $C_{4-9}$ cycloalkyl or $C_{4-9}$ cycloalkenyl;

$R_4$ is selected from optionally substituted heteroaryl, optionally substituted heterocyclyl, or optionally substituted aryl;

$R_5$ is independently selected from hydrogen, or optionally substituted alkyl;

provided that the following compound is excluded:

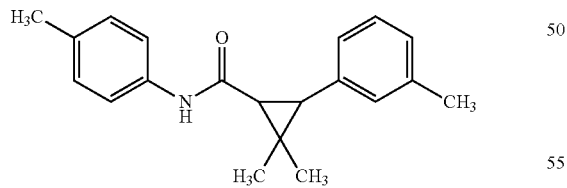

In relation to compounds of formula (I), (Ia), or (Ib) the following definitions may also apply:

a) $R_2$ and $R_3$ are both $C_3$-$C_5$ alkenyl, $C_1$-$C_3$ alkyl (preferably methyl), or Br, or $R_2$ and $R_3$ together form a $C_4$-$C_8$ cycloalkyl ring.

b) $R_2$ and $R_3$ are both $CH_3$.

c) $R_2$ and $R_3$ are both $C_3$-$C_5$ alkenyl.

d) $R_2$ and $R_3$ together form a $C_4$-$C_9$ cycloalkyl ring, preferably cyclopentyl or cyclohexyl ring.

In relation to compounds of formula (I), (Ia) or (II) the following additional definitions may also apply:

e) $R_2$ and $R_3$ are both $C_3$-$C_5$ alkenyl, $C_1$-$C_3$ alkyl (preferably methyl), or Br, or $R_2$ and $R_3$ together form a $C_4$-$C_9$ cycloalkyl ring, and $R_4$ is selected from heteroaryl or aryl each of which may be independently substituted by one to three substituents selected from halogen (in particular, Cl, Br or F), $C_{1-6}$ alkyl, $C_{1-6}$ alkoxy, $C_{2-6}$ alkenyl, $C_{2-6}$ alkynyl, $C_{1-6}$ haloalkyl (in particular —$CF_3$), $C_{1-6}$ haloalkoxy (such as —$OCF_3$), —OH, phenyl, benzyl, phenoxy, benzyloxy, benzoyl, —$NH_2$, —$NHC_{1-4}$ alkyl, —$N(C_{1-4}$ alkyl)$_2$, —CN, —$NO_2$, mercapto, —$S(O)_2NH_2$, —$S(O)_2NHC_{1-4}$ alkyl, —$S(O)_2N(C_{1-4}$ alkyl)$_2$, $C_{1-6}$ alkylcarbonyl, $C_{1-6}$ alkoxycarbonyl, $CO_2H$, —S(O)R''' (where R''' is lower alkyl or cycloalkyl) and —S(O)$_2$R''' (where R''' is lower alkyl, cycloalkyl or OH).

f) $R_2$ and $R_3$ are both $CH_3$, and $R_4$ is selected from heteroaryl or aryl each of which may be independently substituted by one to three substituents selected from halogen (in particular, Cl, Br or F), $C_{1-6}$ alkyl, $C_{1-6}$ alkoxy, $C_{2-6}$ alkenyl, $C_{2-6}$ alkynyl, $C_{1-6}$ haloalkyl (in particular —$CF_3$), $C_{1-6}$ haloalkoxy (such as —$OCF_3$), —OH, phenyl, benzyl, phenoxy, benzyloxy, benzoyl, —$NH_2$, —$NHC_{1-4}$ alkyl, —$N(C_{1-4}$ alkyl)$_2$, —CN, —$NO_2$, mercapto, —$S(O)_2NH_2$, —$S(O)_2NHC_{1-4}$ alkyl, —$S(O)_2N(C_{1-4}$ alkyl)$_2$, $C_{1-6}$ alkylcarbonyl, $C_{1-6}$ alkoxycarbonyl, $CO_2H$, —S(O)R''' (where R''' is lower alkyl or cycloalkyl) and —S(O)$_2$R''' (where R''' is lower alkyl, cycloalkyl or OH).

g) $R_2$ and $R_3$ are both $C_3$-$C_5$ alkenyl, and $R_4$ is selected from heteroaryl or aryl each of which may be independently substituted by one to three substituents selected from halogen (in particular, Cl, Br or F), $C_{1-6}$ alkyl, $C_{1-6}$ alkoxy, $C_{2-6}$ alkenyl, $C_{2-6}$ alkynyl, $C_{1-6}$ haloalkyl (in particular —$CF_3$), $C_{1-6}$ haloalkoxy (such as —$OCF_3$), —OH, phenyl, benzyl, phenoxy, benzyloxy, benzoyl, —$NH_2$, —$NHC_{1-4}$ alkyl, —$N(C_{1-4}$ alkyl)$_2$, —CN, —$NO_2$, mercapto, —$S(O)_2NH_2$, —$S(O)_2NHC_{1-4}$ alkyl, —$S(O)_2N(C_{1-4}$ alkyl)$_2$, $C_{1-6}$ alkylcarbonyl, $C_{1-6}$ alkoxycarbonyl, $CO_2H$, —S(O)R''' (where R''' is lower alkyl or cycloalkyl) and —S(O)$_2$R''' (where R''' is lower alkyl, cycloalkyl or OH).

h) $R_2$ and $R_3$ together form a $C_4$-$C_9$ cycloalkyl ring, preferably cyclopentyl or cyclohexyl ring, and $R_4$ is selected from heteroaryl or aryl each of which may be independently substituted by one to three substituents selected from halogen (in particular, Cl, Br or F), $C_{1-6}$ alkyl, $C_{1-6}$ alkoxy, $C_{2-6}$ alkenyl, $C_{2-6}$ alkynyl, $C_{1-6}$ haloalkyl (in particular —$CF_3$), $C_{1-6}$ haloalkoxy (such as —$OCF_3$), —OH, phenyl, benzyl, phenoxy, benzyloxy, benzoyl, —$NH_2$, —$NHC_{1-4}$ alkyl, —$N(C_{1-4}$ alkyl)$_2$, —CN, —$NO_2$, mercapto, —$S(O)_2NH_2$, —$S(O)_2NHC_{1-4}$ alkyl, —$S(O)_2N(C_{1-4}$ alkyl)$_2$, $C_{1-6}$ alkylcarbonyl, $C_{1-6}$ alkoxycarbonyl, $CO_2H$, —S(O)R''' (where R''' is lower alkyl or cycloalkyl) and —S(O)$_2$R''' (where R''' is lower alkyl, cycloalkyl or OH).

In relation to compounds of formula (Ia) or (Ib) the following additional definitions may also apply:

i) $R_2$ and $R_3$ are both $C_3$-$C_5$ alkenyl, $C_1$-$C_3$ alkyl (preferably methyl), or Br, or $R_2$ and $R_3$ together form a $C_4$-$C_9$ cycloalkyl ring, and $R_4$ is selected from heteroaryl or aryl each of which may be independently substituted by one to three substituents selected from halogen (in particular, Cl, Br or F), $C_{1-6}$ alkyl, $C_{1-6}$ alkoxy, $C_{2-6}$ alkenyl, $C_{2-6}$ alkynyl, $C_{1-6}$ haloalkyl (in particular —$CF_3$), $C_{1-6}$ haloalkoxy (such as —$OCF_3$), —OH, phenyl, benzyl, phenoxy, benzyloxy, benzoyl, —$NH_2$, —$NHC_{1-4}$ alkyl, —N(C$_{1-4}$ alkyl)$_2$, —CN, —NO$_2$, mercapto, —S(O)$_2$NH$_2$, —S(O)$_2$NHC$_{1-4}$ alkyl, —S(O)$_2$N(C$_{1-4}$ alkyl)$_2$, C$_{1-6}$ alkylcarbonyl, C$_{1-6}$ alkoxycarbonyl, CO$_2$H, —S(O)R''' (where R''' is lower alkyl or cycloalkyl) and —S(O)$_2$R''' (where R''' is lower alkyl, cycloalkyl or OH), and n is 0, 1 or 2, and when present, each R$_1$' is independently selected from halogen (in particular, Cl, Br or F), C$_{1-6}$ alkyl, C$_{1-6}$ alkoxy, C$_{2-6}$ alkenyl, C$_{2-6}$ alkynyl, C$_{1-6}$ haloalkyl (in particular —CF$_3$), C$_{1-6}$ haloalkoxy (such as —OCF$_3$), —OH, phenyl, benzyl, phenoxy, benzyloxy, benzoyl, —NH$_2$, —NHC$_{1-4}$ alkyl, —N(C$_{1-4}$ alkyl)$_2$, —CN, —NO$_2$, mercapto, —S(O)$_2$NH$_2$, —S(O)$_2$NHC$_{1-4}$ alkyl, —S(O)$_2$N(C$_{1-4}$ alkyl)$_2$, C$_{1-6}$ alkylcarbonyl, C$_{1-6}$ alkoxycarbonyl, CO$_2$H, —S(O)R''' (where R''' is lower alkyl or cycloalkyl) and —S(O)$_2$R''' (where R''' is lower alkyl, cycloalkyl or OH).

j) R$_2$ and R$_3$ are both CH$_3$, and R$_4$ is selected from heteroaryl or aryl each of which may be independently substituted by one to three substituents selected from halogen (in particular, Cl, Br or F), C$_{1-6}$ alkyl, C$_{1-6}$ alkoxy, C$_{2-6}$ alkenyl, C$_{2-6}$ alkynyl, C$_{1-6}$ haloalkyl (in particular —CF$_3$), C$_{1-6}$ haloalkoxy (such as —OCF$_3$), —OH, phenyl, benzyl, phenoxy, benzyloxy, benzoyl, —NH$_2$, —NHC$_{1-4}$ alkyl, —N(C$_{1-4}$ alkyl)$_2$, —CN, —NO$_2$, mercapto, —S(O)$_2$NH$_2$, —S(O)$_2$NHC$_{1-4}$ alkyl, —S(O)$_2$N(C$_{1-4}$ alkyl)$_2$, C$_{1-6}$ alkylcarbonyl, C$_{1-6}$ alkoxycarbonyl, CO$_2$H, —S(O)R''' (where R''' is lower alkyl or cycloalkyl) and —S(O)$_2$R''' (where R''' is lower alkyl, cycloalkyl or OH), and n is 0, 1 or 2, and when present, each R$_1$' is independently selected from halogen (in particular, Cl, Br or F), C$_{1-6}$ alkyl, C$_{1-6}$ alkoxy, C$_{2-6}$ alkenyl, C$_{2-6}$ alkynyl, C$_{1-6}$ haloalkyl (in particular —CF$_3$), C$_{1-6}$ haloalkoxy (such as —OCF$_3$), —OH, phenyl, benzyl, phenoxy, benzyloxy, benzoyl, —NH$_2$, —NHC$_{1-4}$ alkyl, —N(C$_{1-4}$ alkyl)$_2$, —CN, —NO$_2$, mercapto, —S(O)$_2$NH$_2$, —S(O)$_2$NHC$_{1-4}$ alkyl, —S(O)$_2$N(C$_{1-4}$ alkyl)$_2$, C$_{1-6}$ alkylcarbonyl, C$_{1-6}$ alkoxycarbonyl, CO$_2$H, —S(O)R''' (where R''' is lower alkyl or cycloalkyl) and —S(O)$_2$R''' (where R''' is lower alkyl, cycloalkyl or OH).

k) R$_2$ and R$_3$ are both C$_3$-C$_5$ alkenyl, and R$_4$ is selected from heteroaryl or aryl each of which may be independently substituted by one to three substituents selected from halogen (in particular, Cl, Br or F), C$_{1-6}$ alkyl, C$_{1-6}$ alkoxy, C$_{2-6}$ alkenyl, C$_{2-6}$ alkynyl, C$_{1-6}$ haloalkyl (in particular —CF$_3$), C$_{1-6}$ haloalkoxy (such as —OCF$_3$), —OH, phenyl, benzyl, phenoxy, benzyloxy, benzoyl, —NH$_2$, —NHC$_{1-4}$ alkyl, —N(C$_{1-4}$ alkyl)$_2$, —CN, —NO$_2$, mercapto, —S(O)$_2$NH$_2$, —S(O)$_2$NHC$_{1-4}$ alkyl, —S(O)$_2$N(C$_{1-4}$ alkyl)$_2$, C$_{1-6}$ alkylcarbonyl, C$_{1-6}$ alkoxycarbonyl, CO$_2$H, —S(O)R''' (where R''' is lower alkyl or cycloalkyl) and —S(O)$_2$R''' (where R''' is lower alkyl, cycloalkyl or OH), and n is 0, 1 or 2, and when present, each R$_1$' is independently selected from halogen (in particular, Cl, Br or F), C$_{1-6}$ alkyl, C$_{1-6}$ alkoxy, C$_{2-6}$ alkenyl, C$_{2-6}$ alkynyl, C$_{1-6}$ haloalkyl (in particular —CF$_3$), C$_{1-6}$ haloalkoxy (such as —OCF$_3$), —OH, phenyl, benzyl, phenoxy, benzyloxy, benzoyl, —NHC$_{1-4}$ alkyl, —N(C$_{1-4}$ alkyl)$_2$, —CN, —NO$_2$, mercapto, —S(O)$_2$NH$_2$, —S(O)$_2$NHC$_{1-4}$ alkyl, —S(O)$_2$N(C$_{1-4}$ alkyl)$_2$, C$_{1-6}$ alkylcarbonyl, C$_{1-6}$ alkoxycarbonyl, CO$_2$H, —S(O)R''' (where R''' is lower alkyl or cycloalkyl) and —S(O)$_2$R''' (where R''' is lower alkyl, cycloalkyl or OH).

l) R$_2$ and R$_3$ together form a C$_{4-9}$ cycloalkyl ring, preferably cyclopentyl or cyclohexyl ring, and R$_4$ is selected from heteroaryl or aryl each of which may be independently substituted by one to three substituents selected from halogen (in particular, Cl, Br or F), C$_{1-6}$ alkyl, C$_{1-6}$ alkoxy, C$_{2-6}$ alkenyl, C$_{2-6}$ alkynyl, C$_{1-6}$ haloalkyl (in particular —CF$_3$), C$_{1-6}$ haloalkoxy (such as —OCF$_3$), —OH, phenyl, benzyl, phenoxy, benzyloxy, benzoyl, —NH$_2$, —NHC$_{1-4}$ alkyl, —N(C$_{1-4}$ alkyl)$_2$, —CN, —NO$_2$, mercapto, —S(O)$_2$NH$_2$, —S(O)$_2$NHC$_{1-4}$ alkyl, —S(O)$_2$N(C$_{1-4}$ alkyl)$_2$, C$_{1-6}$ alkylcarbonyl, C$_{1-6}$ alkoxycarbonyl, CO$_2$H, —S(O)R''' (where R''' is lower alkyl or cycloalkyl) and —S(O)$_2$R''' (where R''' is lower alkyl, cycloalkyl or OH), and n is 0, 1 or 2, and when present, each R$_1$' is independently selected from halogen (in particular, Cl, Br or F), C$_{1-6}$ alkyl, C$_{1-6}$ alkoxy, C$_{2-6}$ alkenyl, C$_{2-6}$ alkynyl, C$_{1-6}$ haloalkyl (in particular —CF$_3$), C$_{1-6}$ haloalkoxy (such as —OCF$_3$), —OH, phenyl, benzyl, phenoxy, benzyloxy, benzoyl, —NH$_2$, —NHC$_{1-4}$ alkyl, —N(C$_{1-4}$ alkyl)$_2$, —CN, —NO$_2$, mercapto, —S(O)$_2$NH$_2$, —S(O)$_2$NHC$_{1-4}$ alkyl, —S(O)$_2$N(C$_{1-4}$ alkyl)$_2$, C$_{1-6}$ alkylcarbonyl, C$_{1-6}$ alkoxycarbonyl, CO$_2$H, —S(O)R''' (where R''' is lower alkyl or cycloalkyl) and —S(O)$_2$R''' (where R''' is lower alkyl, cycloalkyl or OH).

In another aspect the invention provides compounds of formula (Ic), or salts thereof:

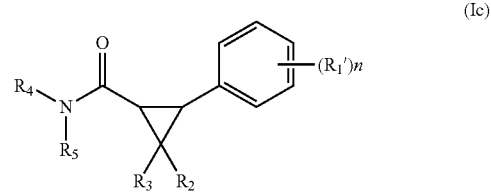

(Ic)

wherein each R$_1$' is independently selected from the group consisting of cyano, halo, nitro, optionally substituted lower alkyl, optionally substituted aryl, optionally substituted aryloxy, optionally substituted arylalkyl, optionally substituted heteroaryl, optionally substituted heterocyclyl, optionally substituted C$_{3-7}$ cycloalkyl, —OR, —C(O)R, —C(O)OR, —OC(O)R (where R is selected from hydrogen, optionally substituted alkyl, optionally substituted alkenyl, optionally substituted alkynyl, optionally substituted C$_{3-7}$ cycloalkyl, optionally substituted heterocyclyl, optionally substituted heteroaryl, and optionally substituted aryl), —C(O)NR'R'', —NR'C(O)R'', —S(O)$_2$—NR'R'' and —NR'R'' (where R' and R'' are independently selected from hydrogen or lower alkyl), —S(O)R''' (where R''' is lower alkyl, or cycloalkyl), —S(O)$_2$R''' (where R''' is lower alkyl, cycloalkyl or OH), or any two adjacent R$_1$' together form heterocyclyl or heteroaryl;

n is 0 or an integer from 1 to 5;

R$_2$ is selected from C$_1$-C$_4$ alkyl, C$_3$-C$_5$ alkenyl, C$_1$-C$_4$ haloalkyl, F, Cl or Br;

R$_3$ is selected from hydrogen, C$_1$-C$_4$ alkyl, C$_3$-C$_5$ alkenyl, C$_1$-C$_4$ haloalkyl, or Br; or R$_2$ and R$_3$ together form C$_{4-9}$ cycloalkyl or C$_{4-9}$ cycloalkenyl;

R$_4$ is selected from heteroaryl which is optionally independently substituted by one to three substituents selected from halogen (in particular, Cl, Br or F), C$_{1-6}$ alkyl, C$_{1-6}$ alkoxy, C$_{2-6}$ alkenyl, C$_{2-6}$ alkynyl, C$_{1-6}$ haloalkyl (in particular —CF$_3$), C$_{1-6}$ haloalkoxy (such as —OCF$_3$), —OH, phenyl, benzyl, phenoxy, benzyloxy, benzoyl, —NH$_2$, —NHC$_{1-4}$ alkyl, —N(C$_{1-4}$ alkyl)$_2$, —CN, —NO$_2$, mercapto, —S(O)$_2$NH$_2$, —S(O)$_2$NHC$_{1-4}$ alkyl, —S(O)$_2$N(C$_{1-4}$ alkyl)$_2$, C$_{1-6}$ alkylcarbonyl, C$_{1-6}$ alkoxycarbonyl, $CO_2H$, —$S(O)R'''$ (where $R'''$ is lower alkyl or cycloalkyl) and —$S(O)_2R'''$ (where $R'''$ is lower alkyl, cycloalkyl or OH); or aryl which is optionally independently substituted by one to three substituents selected from halogen (in particular, Cl, Br or F), $C_{2-6}$ alkyl, $C_{1-6}$ alkoxy, $C_{2-6}$ alkenyl, $C_{2-6}$ alkynyl, $C_{1-6}$ haloalkyl (in particular —$CF_3$), $C_{1-6}$ haloalkoxy (such as —$OCF_3$), —OH, phenyl, benzyl, phenoxy, benzyloxy, benzoyl, —$NH_2$, —$NHC_{1-4}$ alkyl, —$N(C_{1-4}$ alkyl$)_2$, —CN, —$NO_2$, mercapto, —$S(O)_2NH_2$, —$S(O)_2NHC_{1-4}$ alkyl, —$S(O)_2N(C_{1-4}$ alkyl$)_2$, $C_{1-6}$ alkylcarbonyl, $C_{1-6}$ alkoxycarbonyl, $CO_2H$, —$S(O)R'''$ (where $R'''$ is lower alkyl or cycloalkyl) and —$S(O)_2R'''$ (where $R'''$ is lower alkyl, cycloalkyl or OH); and $R_5$ is independently selected from hydrogen, or lower alkyl.

In relation to compounds of formula (II) in an embodiment $R_1$ is an optionally substituted aryl group and more preferably an optionally substituted phenyl group.

Accordingly in another aspect the invention provides compounds of formula (IIa) or salts thereof:

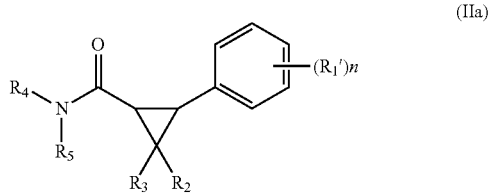

(IIa)

wherein
  each $R_1'$ is independently selected from the group consisting of cyano, halo, nitro, optionally substituted lower alkyl, optionally substituted aryl, optionally substituted aryloxy, optionally substituted arylalkyl, optionally substituted heteroaryl, optionally substituted heterocyclyl, optionally substituted $C_{3-7}$ cycloalkyl, —OR, —C(O)R, —C(O)OR, —OC(O)R (where R is selected from hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl), —C(O)NR'R'', —NR'C(O)R'', —S(O)$_2$—NR'R'' and —NR'R'' (where R' and R'' are independently selected from hydrogen or lower alkyl), —S(O)R''' (where R''' is lower alkyl, or cycloalkyl), —S(O)$_2$R''' (where R''' is lower alkyl, cycloalkyl or OH), or any two adjacent $R_1'$ together form heterocyclyl or heteroaryl;

n is 0 an integer from 1 to 5;

$R_2$ and $R_3$ together form $C_{4-9}$ cycloalkyl;

$R_4$ is selected from optionally substituted heteroaryl, optionally substituted heterocyclyl, or optionally substituted aryl; and $R_5$ is independently selected from hydrogen or optionally substituted alkyl.

Preferably, for compounds of formulae (II) and (IIa) the cycloalkyl ring is $C_4$-$C_7$ or more preferably $C_5$-$C_7$, such as cyclopentyl, cyclohexyl, and cycloheptyl. More preferably the cycloalkyl ring is cyclohexyl or cyclopentyl.

In relation to compounds of formula (IIa) the following definitions may apply:
  m) $R_2$ and $R_3$ together form a cyclohexyl or cyclopentyl ring.
  n) $R_2$ and $R_3$ together form a cyclohexyl or cyclopentyl ring, and $R_4$ is selected from heteroaryl or aryl each of which may be independently substituted by one to three substituents selected from halogen (in particular, Cl, Br or F), $C_{1-6}$ alkyl, $C_{1-6}$ alkoxy, $C_{2-6}$ alkenyl, $C_{2-6}$ alkynyl, $C_{1-6}$ haloalkyl (in particular —$CF_3$), $C_{1-6}$ haloalkoxy (such as —$OCF_3$), —OH, phenyl, benzyl, phenoxy, benzyloxy, benzoyl, —$NH_2$, —$NHC_{1-4}$ alkyl, —$N(C_{1-4}$ alkyl$)_2$, —CN, —$NO_2$, mercapto, —$S(O)_2NH_2$, —$S(O)_2NHC_{1-4}$ alkyl, —$S(O)_2N(C_{1-4}$ alkyl$)_2$, $C_{1-6}$ alkylcarbonyl, $C_{1-6}$ alkoxycarbonyl, $CO_2H$, —$S(O)_2R'''$ (where $R'''$ is lower alkyl or cycloalkyl) and —$S(O)_2R'''$ (where $R'''$ is lower alkyl, cycloalkyl or OH).
  o) $R_2$ and $R_3$ together form a cyclohexyl or cyclopentyl ring, and $R_4$ is selected from heteroaryl or aryl each of which may be independently substituted by one to three substituents selected from halogen (in particular, Cl, Br or F), $C_{1-6}$ alkyl, $C_{1-6}$ alkoxy, $C_{2-6}$ alkenyl, $C_{2-6}$ alkynyl, $C_{1-6}$ haloalkyl (in particular —$CF_3$), $C_{1-6}$ haloalkoxy (such as —$OCF_3$), —OH, phenyl, benzyl, phenoxy, benzyloxy, benzoyl, —$NH_2$, —$NHC_{1-4}$ alkyl, —$N(C_{1-4}$ alkyl$)_2$, —CN, —$NO_2$, mercapto, —$S(O)_2NH_2$, —$S(O)_2NHC_{1-4}$ alkyl, —$S(O)_2N(C_{1-4}$ alkyl$)_2$, $C_{1-6}$ alkylcarbonyl, $C_{1-6}$ alkoxycarbonyl, $CO_2H$ and sulfone (in particular —$S(O)_2C_{1-4}$ alkyl), and n is 0, 1 or 2, and when present, each $R_1'$ is independently selected from halogen (in particular, Cl, Br or F), $C_{1-6}$ alkyl, $C_{1-6}$ alkoxy, $C_{2-6}$ alkenyl, $C_{2-6}$ alkynyl, $C_{1-6}$ haloalkyl (in particular —$CF_3$), $C_{1-6}$ haloalkoxy (such as —$OCF_3$), —OH, phenyl, benzyl, phenoxy, benzyloxy, benzoyl, —$NH_2$, —$NHC_{1-4}$ alkyl, —$N(C_{1-4}$ alkyl$)_2$, —CN, —$NO_2$, mercapto, —$S(O)_2NH_2$, —$S(O)_2NHC_{1-4}$ alkyl, —$S(O)_2N(C_{1-4}$ alkyl$)_2$, $C_{1-6}$ alkylcarbonyl, $C_{1-6}$ alkoxycarbonyl, $CO_2H$, —$S(O)R'''$ (where $R'''$ is lower alkyl or cycloalkyl) and —$S(O)_2R'''$ (where $R'''$ is lower alkyl, cycloalkyl or OH).

In relation to compounds of formula (Ia), (Ib), or (IIa) one or more of the following preferred definitions (where appropriate) may also apply:
  p) each $R_1'$ is independently selected from $C_1$-$C_3$ alkoxy, $C_1$-$C_3$ alkyl, halo (preferably Cl, F, or Br), $S(O)_2NR'R''$ (where R' and R'' are independently hydrogen or $C_1$-$C_3$ alkyl), optionally substituted heteroaryl, $CF_3$, boronic ester, or $S(O)_2R'''$ where $R'''$ is lower alkyl;
  q) $R_5$ is H.

In a further embodiment and reference to any one of formula (I), (Ia), (Ib), (Ic), (II) or (IIa), the following additional preferred definitions may also apply.

$R_4$ is selected from:

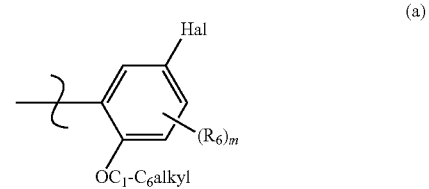

(a)

wherein
  Hal is a halogen;
  m is 0, 1 or 2; and
  each $R_6$ is independently selected from halogen, hydroxy, CN, $NO_2$, haloalkyl, aryl, heteroaryl, $C_{1-3}$ alkoxy, $C_{1-3}$ alkyl, or $CO_2R'$ (where R' is a lower alkyl or H);

or (b) a heteroaryl substituted from 1 to 3 times from a group selected from $C_1$-$C_3$ alkyl, $C_{1-6}$ alkoxy, $C_{2-6}$ alkenyl, $C_{2-6}$ alkynyl, $C_{1-6}$ haloalkyl (in particular —$CF_3$), $C_{1-6}$ haloalkoxy (such as —$OCF_3$), —OH, phenyl, benzyl, phenoxy, benzyloxy, benzoyl, —$NH_2$, —$NHC_{1-4}$ alkyl, —$N(C_{1-4}$ alkyl$)_2$, —CN, —$NO_2$, mercapto, $C_{1-6}$ alkylcarbonyl, $C_{1-6}$ alkoxycarbonyl, $CO_2H$, —S(O)R''' (where R''' is lower alkyl or cycloalkyl) and —S(O)$_2$R''' (where R''' is lower alkyl, cycloalkyl or OH). Preferred heteroaryl groups for $R_4$ include pyridinyl, pyrazolyl and thiazolyl.

In yet a further embodiment and with reference to formulae (I) and (II):

$R_1$ is phenyl; phenyl independently substituted by one or two substituents selected from halogen, —$SO_2NR'R''$ (where R' and R'' independently represent H or lower alkyl), $C_{1-4}$ alkoxy, or $C_{1-4}$ alkyl; heterocyclyl or heteroaryl;

$R_2$ and $R_3$ are the same and represent $C_{1-4}$ alkyl, (formula (I)) or together a $C_5$-$C_6$ cycloalkyl (formula (I) and formula (II));

$R_4$ is heteroaryl or heteroaryl independently substituted one or two times by $C_{1-4}$ alkyl, $C_{1-4}$ haloalkyl, halogen, or $C_{1-4}$ alkoxy; or is phenyl or phenyl independently substituted one or two times by $C_{1-4}$ alkyl, $C_{1-4}$ haloalkyl, halogen, or $C_{1-4}$ alkoxy; and $R_5$ is H or lower alkyl.

In the list below (which are representative examples of compounds of the present invention) the structures contain one or more stereogenic centers, the respective structures are depicted in an arbitrary absolute configuration. These structures also include the respective structure having the opposite stereochemistry and the corresponding racemate:

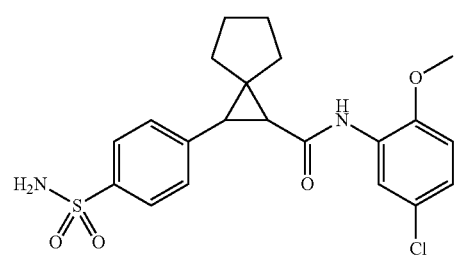

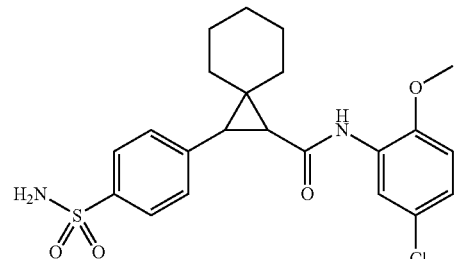

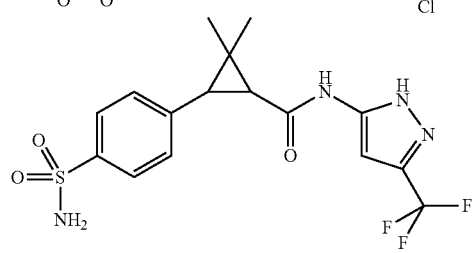

-continued

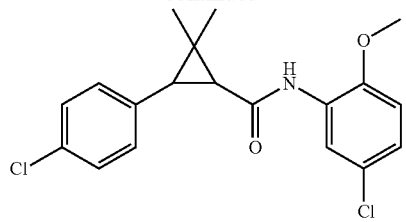

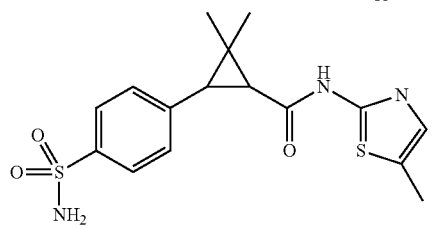

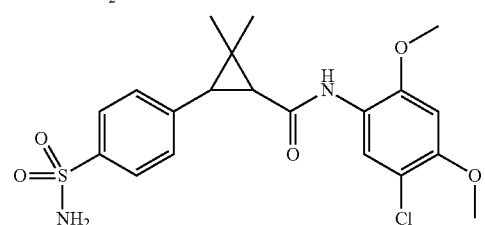

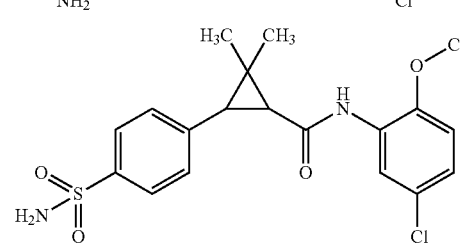

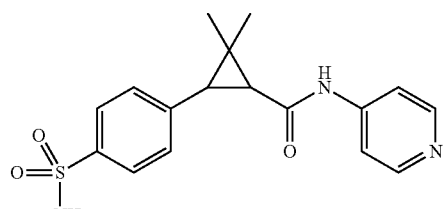

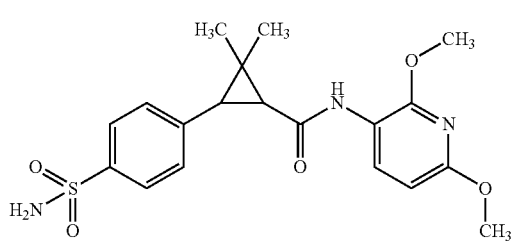

-continued
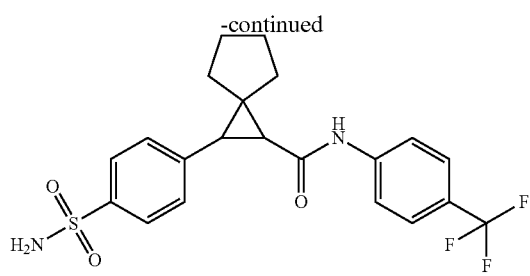
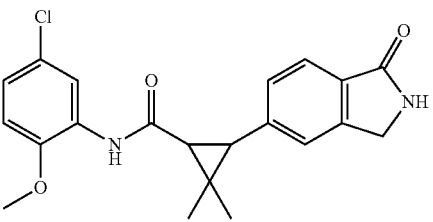
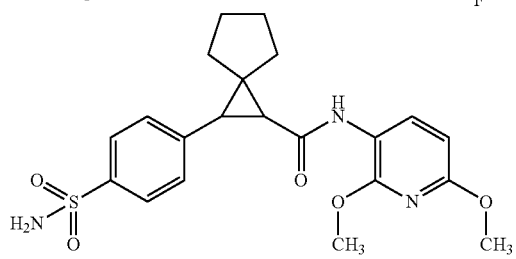
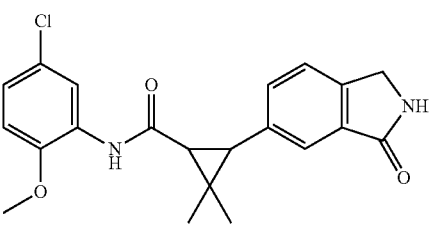
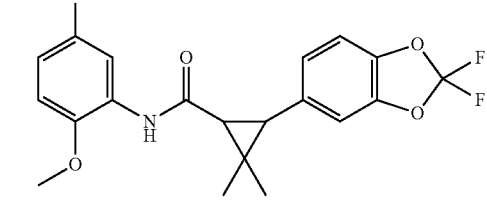
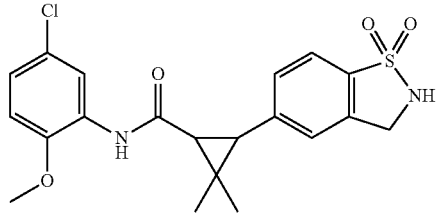
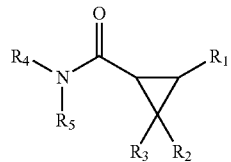
In certain embodiments, the compounds are selected from those depicted below:
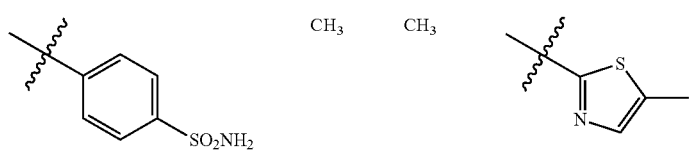
(I)
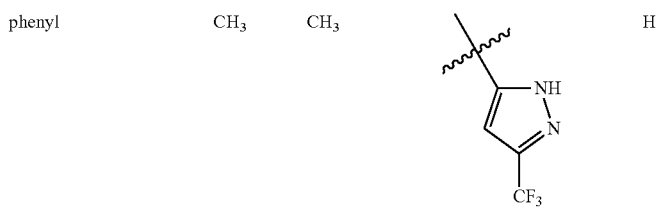
| R₁ | R₂ | R₃ | R₄ | R₅ |
|---|---|---|---|---|
| phenyl | CH₃ | CH₃ | 2-(5-methylthiazolyl) | H |
| 4-(SO₂NH₂)phenyl | CH₃ | CH₃ | 2-(5-methylthiazolyl) | H |
| phenyl | CH₃ | CH₃ | 5-(3-CF₃-1H-pyrazolyl) | H |

-continued
| R₁ | R₂ | R₃ | R₄ | R₅ |
|---|---|---|---|---|
| 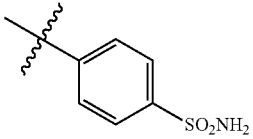 [SMILES: *c1ccc(S(N)(=O)=O)cc1] 4-sulfamoylphenyl | CH₃ | CH₃ | 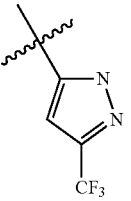 5-(trifluoromethyl)-1H-pyrazol-3-yl | H |
| phenyl | CH₃ | CH₃ | 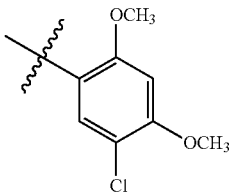 [SMILES: *c1cc(Cl)c(OC)cc1OC] 5-chloro-2,4-dimethoxyphenyl | H |
| 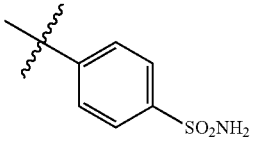 4-sulfamoylphenyl | CH₃ | CH₃ | 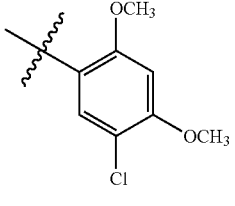 [SMILES: *c1cc(Cl)c(OC)cc1OC] 5-chloro-2,4-dimethoxyphenyl | H |
| phenyl | CH₃ | CH₃ | 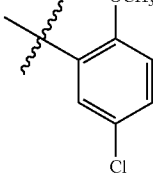 5-chloro-2-methoxyphenyl | H |
| 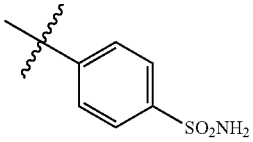 4-sulfamoylphenyl | CH₃ | CH₃ | 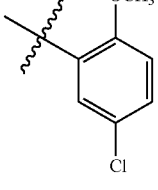 5-chloro-2-methoxyphenyl | H |
| 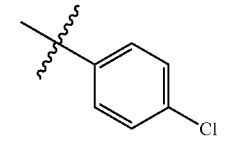 [SMILES: *c1ccc(Cl)cc1] 4-chlorophenyl | CH₃ | CH₃ | 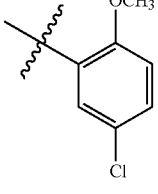 5-chloro-2-methoxyphenyl | H |
| phenyl | cyclopentyl | | 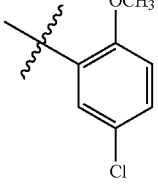 5-chloro-2-methoxyphenyl | H |

-continued

| R₁ | R₂ | R₃ | R₄ | R₅ |
|---|---|---|---|---|
| 4-(SO₂NH₂)phenyl | | cyclopentyl | 2-OCH₃-5-Cl-phenyl | H |
| phenyl | | cyclohexyl | 2-OCH₃-5-Cl-pyridin-3-yl | H |
| 4-(SO₂NH₂)phenyl | | cyclohexyl | 2-OCH₃-5-Cl-phenyl | H |
| phenyl | | cyclopentyl | 2,6-di(OCH₃)-pyridin-3-yl | H |
| 4-(SO₂NH₂)phenyl | | cyclopentyl | 2,6-di(OCH₃)-pyridin-3-yl | H |
| phenyl | | cyclopentyl | 4-CF₃-phenyl | H |
| 4-(SO₂NH₂)phenyl | | cyclopentyl | 4-CF₃-phenyl | H |
| phenyl | CH₃ | CH₃ | pyridin-4-yl | H |
| 4-(SO₂NH₂)phenyl | CH₃ | CH₃ | pyridin-4-yl | H |

-continued

| R₁ | R₂ | R₃ | R₄ | R₅ |
|---|---|---|---|---|
| 4-(SO₂N(CH₃)₂)phenyl | CH₃ | CH₃ | 2-OCH₃, 5-Cl phenyl | H |
| 4-Br phenyl | CH₃ | CH₃ | 2-OCH₃, 5-Cl phenyl | H |
| phenyl | CH₃ | CH₃ | 2-OCH₃ pyridin-3-yl | H |
| 4-(SO₂NH₂)phenyl | CH₃ | CH₃ | 2-OCH₃ pyridin-3-yl | H |
| phenyl | CH₂CH₃ | CH₂CH₃ | 2-OCH₃, 5-Cl phenyl | H |
| 4-(SO₂NH₂)phenyl | CH₂CH₃ | CH₂CH₃ | 2-OCH₃, 5-Cl phenyl | H |
| phenyl | cyclopentyl |  | 2-Cl, 4-CF₃ phenyl | H |
| 4-(SO₂NH₂)phenyl |  | cyclopentyl | 2-Cl, 4-CF₃ phenyl | H |

-continued

| R₁ | R₂ | R₃ | R₄ | R₅ |
|---|---|---|---|---|
| 3-methylphenyl | CH₃ | CH₃ | 3,4-difluorophenyl | H |
| 4-methyl-3-(SO₂NH₂)phenyl (methyl at 2, SO₂NH₂ at 4) | CH₃ | CH₃ | 3,4-difluorophenyl | H |
| 3-methylphenyl | CH₃ | CH₃ | 2-methoxy-4-chlorophenyl | H |
| 4-methyl-3-(SO₂NH₂)phenyl | CH₃ | CH₃ | 2-methoxy-4-chlorophenyl | H |
| 2,2-difluoro-1,3-benzodioxol-5-yl | CH₃ | CH₃ | 2-methoxy-4-chlorophenyl | H |

The salts of the compounds of the invention are preferably pharmaceutically acceptable, but it will be appreciated that non-pharmaceutically acceptable salts also fall within the scope of the present invention, since these are useful as intermediates in the preparation of pharmaceutically acceptable salts.

It will be appreciated that the compounds of the invention, and the salts thereof, can be presented in the form of pharmaceutically acceptable derivatives. The term "pharmaceutically acceptable derivative" includes pharmaceutically acceptable esters, prodrugs, solvates and hydrates of the compounds of formulae (I), (Ia), (Ib), (Ic), (II), or (IIa), or salts thereof. Pharmaceutically acceptable derivatives may include any pharmaceutically acceptable hydrate or any other compound or prodrug which, upon administration to a subject, is capable of providing (directly or indirectly) a compound of formula (I), (Ia), (Ib), (Ic), (II), or (IIa), or an active metabolite or residue thereof.

The pharmaceutically acceptable salts include acid addition salts, base addition salts, and the salts of quaternary amines and pyridiniums. The acid addition salts are formed from a compound of the invention and a pharmaceutically acceptable inorganic or organic acid including but not limited to hydrochloric, hydrobromic, sulfuric, phosphoric, methanesulfonic, toluenesulphonic, benzenesulphonic, acetic, propionic, ascorbic, citric, malonic, fumaric, maleic, lactic, salicylic, sulfamic, or tartaric acids. The counter ion of quaternary amines and pyridiniums include chloride, bromide, iodide, sulfate, phosphate, methansulfonate, citrate, acetate, malonate, fumarate, sulfamate, and tartrate. The base addition salts include but are not limited to salts such as sodium, potassium, calcium, lithium, magnesium, ammonium and alkylammonium. Also, basic nitrogen-containing groups may be quaternised with such agents as lower alkyl halides, such as methyl, ethyl, propyl, and butyl chlorides, bromides and iodides; dialkyl sulfates like dimethyl and diethyl sulfate; and others. The salts may be made in a known manner, for example by treating the compound with an appropriate acid or base in the presence of a suitable solvent.

The compounds of the invention may be in crystalline form and/or as solvates (e.g. hydrates) and it is intended that both forms be within the scope of the present invention. The term "solvate" is a complex of variable stoichiometry formed by a solute (in this invention, a compound of the invention) and a solvent. Such solvents should not interfere with the biological activity of the solute. Solvents may be, by way of example, water, ethanol or acetic acid. Methods of solvation are generally known within the art.

The term "pro-drug" is used in its broadest sense and encompasses those derivatives that are converted in vivo to the compounds of the invention. Such derivatives would readily occur to those skilled in the art, and include, for example, compounds where a free hydroxy group is converted into an ester derivative or a ring nitrogen atom is converted to an N-oxide. Examples of ester derivatives include alkyl esters, phosphate esters and those formed from amino acids, preferably valine. Any compound that is a prodrug of a compound of the invention is within the scope and spirit of the invention.

The term "pharmaceutically acceptable ester" includes biologically acceptable esters of compound of the invention such as sulphonic, phosphonic and carboxylic acid derivatives.

Thus, in another aspect of the invention, there is provided a prodrug or pharmaceutically acceptable ester of a compound of the invention or of salt thereof.

It will be appreciated that the compounds of the invention have at least one asymmetric centre, and therefore are capable of existing in more than one stereoisomeric form. The invention extends to each of these forms individually and to mixtures thereof, including racemates. The isomers may be separated conventionally by chromatographic methods or using a resolving agent. Alternatively the individual isomers may be prepared by asymmetric synthesis using chiral intermediates. Where the compound has at least one carbon-carbon double bond, it may occur in Z- and E-forms with all isomeric forms of the compounds being included in the present invention.

The invention also includes where possible a salt or pharmaceutically acceptable derivative such as a pharmaceutically acceptable ester, solvate and/or prodrug of the above mentioned embodiments of the invention.

In another aspect of the invention, there is provided a pharmaceutical composition that comprises a therapeutically effective amount of one or more of the aforementioned compounds or pharmaceutically acceptable salts thereof, including pharmaceutically acceptable derivatives thereof, and optionally a pharmaceutically acceptable carrier or diluent.

In another aspect, the present invention provides pharmaceutical compositions for use as a positive allosteric modulator of α7nAChRs, more particularly as an anti-inflammatory or neuroprotective agent, the composition comprising an effective amount of a compound of Formula (I), (Ia), (Ib), (Ic), (II), or (IIa), or a pharmaceutically acceptable salt thereof, including a pharmaceutically acceptable derivative thereof, and optionally a pharmaceutically acceptable carrier or diluent.

The term "composition" is intended to include the formulation of an active ingredient with encapsulating material as carrier, to give a capsule in which the active ingredient (with or without other carrier) is surrounded by carriers.

The pharmaceutical compositions or formulations include those suitable for oral, rectal, nasal, topical (including buccal and sub-lingual), vaginal or parenteral (including intramuscular, sub-cutaneous and intravenous) administration or in a form suitable for administration by inhalation or insufflation.

The compounds of the invention, together with a conventional adjuvant, carrier, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use.

Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Formulations containing ten (10) milligrams of active ingredient or, more broadly, 0.1 to one hundred (100) milligrams, per tablet, are accordingly suitable representative unit dosage forms.

The compounds of the present invention can be administered in a wide variety of oral and parenteral dosage forms. It will be obvious to those skilled in the art that the following dosage forms may comprise, as the active component, either a compound of the invention or a pharmaceutically acceptable salt of a compound of the invention.

For preparing pharmaceutical compositions from the compounds of the present invention, pharmaceutically acceptable carriers can be either solid or liquid. Solid form preparations include powders, tablets, pills, capsules, cachets, suppositories, and dispensable granules. A solid carrier can be one or more substances which may also act as diluents, flavouring agents, solubilisers, lubricants, suspending agents, binders, preservatives, tablet disintegrating agents, or an encapsulating material.

In powders, the carrier is a finely divided solid that is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as an admixture of fatty acid glycerides or cocoa butter, is first melted and the active component is dispersed homogeneously therein, as by stirring. The molten homogenous mixture is then poured into convenient sized moulds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution.

Sterile liquid form compositions include sterile solutions, suspensions, emulsions, syrups and elixirs. The active ingredient can be dissolved or suspended in a pharmaceutically acceptable carrier, such as sterile water, sterile organic solvent or a mixture of both.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilisation from solution, for constitution with a suitable vehicle, eg. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilising agents, and the like.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Formulations suitable for topical administration in the mouth include lozenges comprising active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multidose form. In the latter case of a dropper or pipette, this may be achieved by the patient administering an appropriate, predetermined volume of the solution or suspension. In the case of a spray, this may be achieved for example by means of a metering atomising spray pump. To improve nasal delivery and retention the compounds according to the invention may be encapsulated with cyclodextrins, or formulated with other agents expected to enhance delivery and retention in the nasal mucosa.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In formulations intended for administration to the respiratory tract, including intranasal formulations, the compound will generally have a small particle size for example of the order of 5 to 10 microns or less. Such a particle size may be obtained by means known in the art, for example by micronisation.

When desired, formulations adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The invention also includes the compounds in the absence of carrier where the compounds are in unit dosage form.

The amount of the compound of the invention to be administered may be in the range from about 10 mg to 2000 mg per day, depending on the activity of the compound and the disease to be treated.

Liquids or powders for intranasal administration, tablets or capsules for oral administration and liquids for intravenous administration are the preferred compositions.

The pharmaceutical preparations of the compounds according to the present invention may be co-administered with one or more other active agents in combination therapy. For example the pharmaceutical preparation of the active compound may be co-administered (for example, separately, concurrently or sequentially), with one or more other agents used to treat cognitive impairment or mood disorders such as acetylcholine esterase inhibitors, antipsychotics, and antidepressants.

It is believed that the compounds of the invention may be beneficial in treating patients with cognition impairment or aid in increasing cognition. Without wanting to be bound by theory it is believed that this effect may be brought about by positive allosteric modulation of alpha 7 nicotinic acetylcholine receptors ($\alpha$7nAChRs).

It is envisaged that the compounds may additionally be useful in the treatment of patients, including a mammal and especially a human, suffering from neuropsychiatric diseases and neurodegenerative diseases involving a dysfunction of the cholinergic system, and further conditions of memory and/or cognition impairment, including, for example, schizophrenia, anxiety, mania, depression, manic depression (as examples of neuropsychiatric disorders), Tourette's syndrome, Parkinson's disease, Huntington's disease (as examples of neurodegenerative diseases), and/or cognitive disorders (such as Alzheimer's disease, Lewy Body Dementia, Amyotrophic Lateral Sclerosis, memory impairment, memory loss, cognition deficit, attention deficit, Attention Deficit Hyperactivity Disorder).

Neurodegenerative disorders include, but are not limited to, treatment and/or prophylaxis of Alzheimer's diseases, Pick's disease, diffuse Lewy Body disease, progressive supranuclear palsy (or Steel-Richardson syndrome), multisystem degeneration (or Shy-Drager syndrome), motor neuron diseases including amyotrophic lateral sclerosis, degenerative ataxias, cortical basal degeneration, ALS-Parkinson's-Dementia complex of Guam, subacute sclerosing panencephalitis, Huntington's disease, Parkinson's disease, synucleinopathies, primary progressive aphasia, striatonigral degeneration, Machado-Joseph disease/spinocerebellar ataxia type 3, olivopontocerebellar degenerations, Gilles De La Tourette's disease, bulbar, pseudobulbar palsy, spinal muscular atrophy, spinobulbar muscular atrophy (Kennedy's disease), primary lateral sclerosis, familial spastic paraplegia, Werdnig-Hoffmann disease, Kugelberg-Welander disease, Tay-Sach's disease, Sandhoff disease, familial spastic disease, Wohlfart-Kugelberg-Welander disease, spastic paraparesis, progressive multifocal leukoencephalopathy, prion diseases (such as Creutzfeldt-Jakob, Gerstmann-Straussler-Scheinker disease, Kuru and fatal familial insomnia), and neurodegenerative disorders resulting from cerebral ischemia or infarction including embolic occlusion and thrombotic occlusion as well as intracranial hemorrhage of any type (including, but not limited to, epidural, subdural, subarachnoid and intracerebral), and intracranial and intravertebral lesions (including, but not limited to, contusion, penetration, shear, compression and laceration).

In addition, the compounds of the invention may be used to treat age-related dementia and other dementias and conditions with memory loss including age-related memory loss, senility, vascular dementia, diffuse white matter disease (Binswanger's disease), dementia of endocrine or metabolic origin, dementia of head trauma and diffuse brain damage, dementia pugilistica and frontal lobe dementia.

The invention provides methods of treating subjects suffering from memory impairment due to, for example, Alzheimer's disease, mild cognitive impairment due to aging, schizophrenia, Parkinson's disease, multiple sclerosis, Huntington's disease, Pick's disease, Creutzfeldt-Jakob disease, depression, aging, head trauma, stroke, CNS hypoxia, cerebral senility, multiinfarct dementia and other neurological conditions, as well as HIV and cardiovascular diseases.

For certain of the abovementioned conditions it is clear that the compounds may be used prophylactically as well as for the alleviation of symptoms.

References herein to "treatment" or the like are to be understood to include such prophylactic treatment, as well as therapeutic treatments.

The compounds of the present invention as agents which modulate the α7 nAChR may be particularly useful in the therapeutic or prophylactic treatment of diseases such as schizophrenia, bi-polar disorder, anxiety, AD, ADHD, mild cognitive impairment, Parkinson's Disease, Huntington's disease, Tourette's syndrome, brain trauma, jetlag and nicotine addiction, Accordingly in a further aspect of the invention, there is provided a means for ameliorating the cognitive deficits associated with neurodegenerative and neuropsychiatric diseases and also inflammatory diseases by the application of a positive allosteric modulators of α7nAChRs selected from a compound of Formula (I), (Ia), (Ib), (Ic), (II), or (IIa), or salt thereof, including a pharmaceutically acceptable derivative thereof, or a composition comprising the compound of Formula (I), (Ia), (Ib), (Ic), (II), or (IIa), or salt thereof, or a pharmaceutically acceptable derivative thereof.

In another aspect of the invention a method is provided for preventing or treating cognitive deficits involving dysfunction of the cholinergic system including the step of administrating a compound of Formula (I), (Ia), (Ib), (Ic), (II), or (IIa), or salt thereof, or a composition comprising the compound or salt thereof.

In another preferred form of the invention there is provided a method for preventing or treating neurodegenerative or neuropsychiatric disorders including the step of administrating a compound of Formula (I), (Ia), (Ib), (Ic), (II), or (IIa), or a pharmaceutically acceptable salt thereof, including a pharmaceutically acceptable derivative thereof, or a composition comprising the compound or pharmaceutically acceptable salt thereof, or pharmaceutically acceptable derivative thereof.

In a further aspect of the present invention, there is provided the use of a compound of Formula (I), (Ia), (Ib), (Ic), (II), or (IIa), or salt thereof, in the preparation of a medicament for the treatment (therapeutic or prophylactic) of disease states in which modulation of α7nAChRs would be beneficial.

In a further aspect of the invention there is provided a process for the production of the compounds of Formula (I), (Ia), (Ib), (Ic), (II), or (IIa), or salts thereof, including pharmaceutically acceptable derivatives thereof.

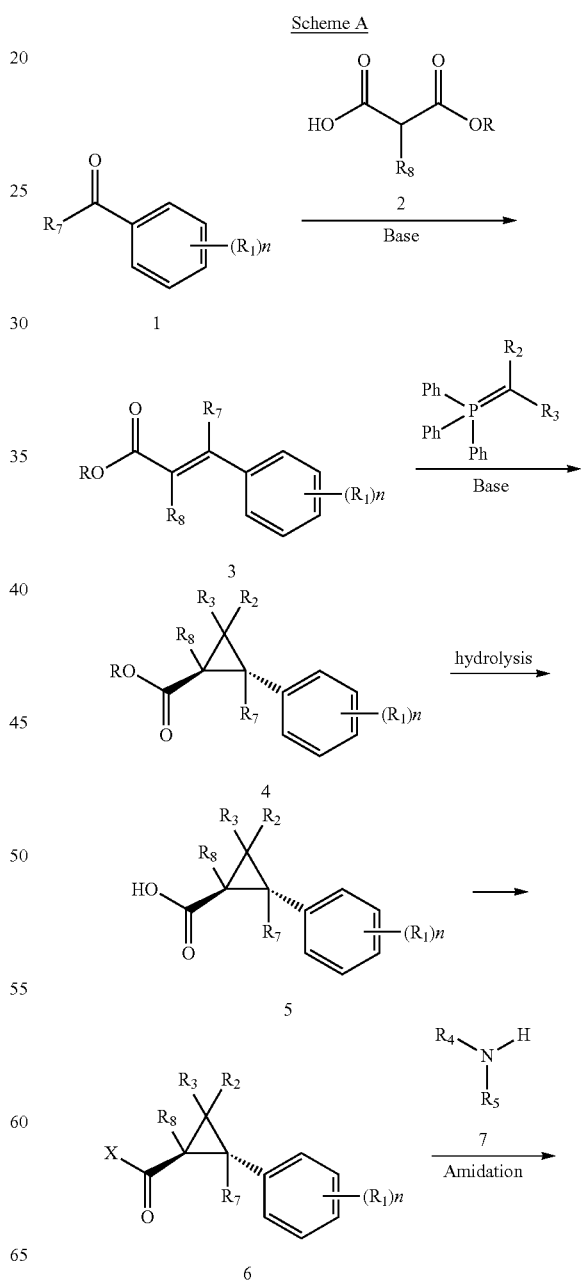

-continued

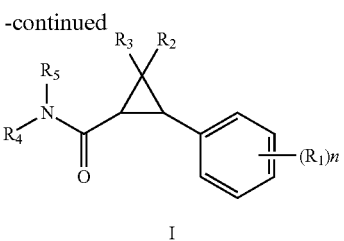

I

Compounds of the formula I can be prepared by synthetic procedures as depicted in Scheme A. Cinnamate esters 1 may be from commercial sources or prepared by Doebner modification of Knoevenagel condensation of an aryl/heteroaryl aldehyde. Typically, an aryl/heteroaryl aldehyde 1 and ester of malonic acid 2 is heated in pyridine/piperidine mixture. Numerous modification of this procedure as well as other alternatives such as Aldol-type condensation or Wittig reaction of aryl or heteroaryl carbonyl compounds are possible and will be readily apparent to those skilled in the art. Cyclopropanation of olefin was carried out by reacting cinnamate ester 3 with phosphorus ylides as described in *J. Med. Chem.* 2001, 44, 3302. The requisite ylides can be purchased or prepared by known methods. Those skilled in the art will understand that cyclopropanation of olefins could be achieved by alternative methods, such as Simmons-Smith type reaction of cinnamate ester with Furukawa reagents as described in *Tetrahedron* 1969, 25, 2647 or ring forming reaction of cinnamate ester with sulphur ylides as described in *Synthesis* 2008, 20, 3279. Ester 4 where $R_2$ and $R_3$ are bromo or chloro can be prepared by heating a mixture of cinnamate ester 3 and ethyl trihaloacetate as depicted in Scheme B. Numerous modifications of this procedure such as use of trihaloacetic acid in acetic anhydride as described in *J. Org. Chem.* 1988, 53, 4945 are possible and will be readily apparent to those skilled in the art. Similarly, ester 4 where $R_2$ and $R_3$ are fluoro can be prepared by heating cinnamate 3 with a difluoro carbine generated from suitable reagent such as trimethylsilyl fluorosulfonyldifluoroacetate as described in *J. Fluorine Chem.* 2004, 125, 459.

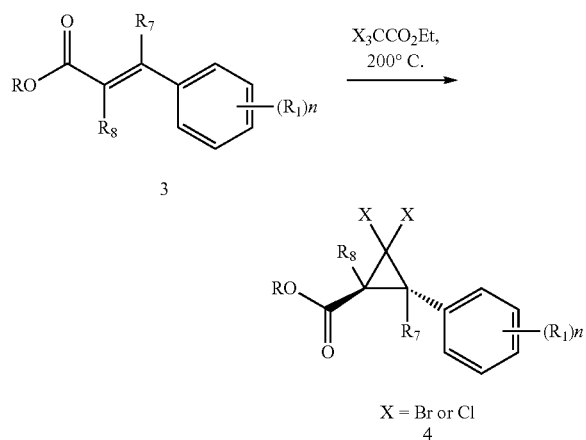

Esters 4 where $R_2$ and $R_3$ together form a cycloalkyl or cycloalkenyl group can be prepared by from corresponding Spiro group containing phosphorus ylides. Alternatively, phosphorus ylides where $R_2$ and $R_3$ contains terminal alkene group can be reacted with cinnamate esters, followed by ring-closure metathesis as described in *J. Chem. Res.* 2006, 9, 591 to form ester 4 where $R_2$ and $R_3$ together form cycloalkenyl group, which could be further reduced to form corresponding cycloalkyl group containing ester 4. Ester 4 can be hydrolysed to acid 5 by using known procedures and then reacted with thionyl chloride to offer acid chloride 6 where X is Cl. The acid chloride can be then reacted with amine to offer compounds of formula I. Numerous alternative amide formation procedures could be used such as direct coupling of acid with amine in presence of dicyclohexyldiimide or other diimides, conversion of acid to reactive anhydride and then coupling with amine. Compounds of formula I where $R_1$ is —$SO_2NH_2$ may be prepared by Freidel-Crafts sulphonation of compound I where $R_1$ is H with $ClSO_2OH$ in DCM followed reaction with ammonia as described in *Synthetic Communications* 1994, 24, 671. Those skilled in the art will understand that various modifications of this procedure such as replacement of $ClSO_2OH$ with thionyl chloride or $ClSO_2$-alkyl or $ClSO_2NH_2$ as described in *Chemische Berichte* 1959, 92, 509 could be used to prepare corresponding sulphonamide/sulphone derivatives. Also, compounds of formula I where $R_1$ is halogen can be prepared by using halogenated starting material compound 3 where $R_1$ is halogen or halogenation of compound I where $R_1$ is H as depicted in scheme C. The halogenated material can further be functionalised using known chemistry such as Suzuki coupling, Sonogashira coupling etc.

Scheme C

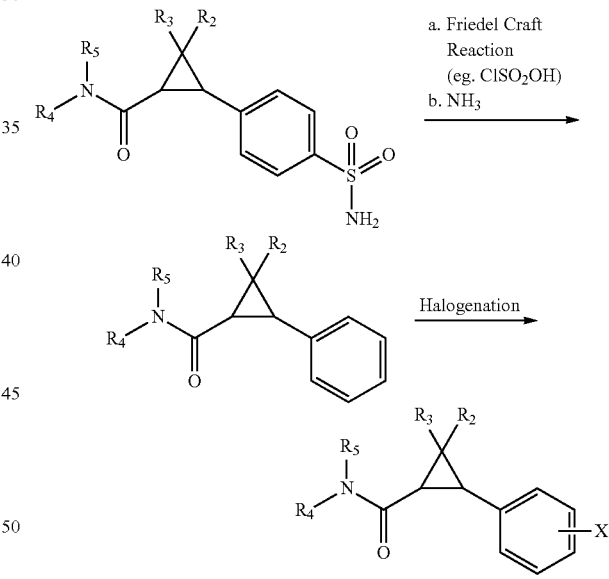

Another variation is to add, remove or modify the substituents of the product to form new derivatives. This could be achieved again by using standard techniques for functional group inter-conversion, well known in the industry such as those described in Comprehensive organic transformations: a guide to functional group preparations by Larock R C, New York, VCH Publishers, Inc. 1989.

Examples of possible functional group inter-conversions are: —C(O)NRR' from —$CO_2CH_3$ by heating with or without catalytic metal cyanide, e.g. NaCN, and HNRR' in $CH_3OH$; —OC(O)R from —OH with e.g., ClC(O)R' in pyridine; —NR—C(S)NR'R" from —NHR with an alkylisothiocyanate or thiocyanic acid; —NRC(O)OR from —NHR with alkyl chloroformate; —NRC(O)NR'R" from —NHR by treatment with an isocyanate, e.g. HN=C=O or RN=C=O; —NRC(O)R' from —NHR by treatment with ClC(O)R' in pyridine; —C(=NR)NR'R" from —C(NR'R")SR'" with $H_3NR^+$ $OAc^-$ by heating in alcohol; —C(NR'R")SR from —C(S)NR'R" with R—I in an inert solvent, e.g. acetone; —C(S)NR'R" (where R' or R" is not hydrogen) from —C(S)$NH_2$ with HNR'R"; —C(=NCN)—NR'R" from —C(=NR'R")—SR with $NH_2$CN by heating in anhydrous alcohol, alternatively from —C(=NH)—NR'R" by treatment with BrCN and NaOEt in EtOH; —NR—C(=NCN)SR from —NHR' by treatment with $(RS)_2$C=NCN; —NR"$SO_2$R from —NHR' by treatment with $ClSO_2$R by heating in pyridine; —NR'C(S)R from —NR'C(O)R by treatment with Lawesson's reagent [2,4-bis(4-methoxyphenyl)-1,3,2,4-dithiadiphosphetane-2,4-disulfide]; —NR$SO_2CF_3$ from —NHR with triflic anhydride and base, —CH($NH_2$)CHO from —CH($NH_2$)C(O)OR' with Na(Hg) and HCl/EtOH; —$CH_2$C(O)OH from —C(O)OH by treatment with $SOCl_2$ then $CH_2N_2$ then $H_2O/Ag_2O$; —C(O)OH from —$CH_2$C(O)$OCH_3$ by treatment with PhMgX/HX then acetic anhydride then $CrO_3$; R—OC(O)R' from RC(O)R' by R"$CO_3$H; —$CCH_2$OH from —C(O)OR' with Na/R'OH; —$CHCH_2$ from —$CH_2CH_2$OH by the Chugaev reaction; —$NH_2$ from —C(O)OH by the Curtius reaction; —$NH_2$ from —C(O)NHOH with TsCl/base then $H_2$O; —CHC(O)CHR from —CHCHOHCHR by using the Dess-Martin Periodinane regent or $CrO_3$/aq$H_2SO_4$/acetone; —$C_6H_5$CHO from —$C_6H_5CH_3$ with $CrO_2Cl_2$; —CHO from —CN with $SnCl_2$/HCl; —CN from —C(O)NHR with $PCl_5$; —$CH_2$R from —C(O)R with $N_2H_4$/KOH; —S(O)$_2$R from —SR with mCPBA.

In order that the present invention may be more readily understood, we provide the following non-limiting examples.

EXAMPLES

General Procedure

All anhydrous solvents were commercially obtained and stored in Sure-Seal bottles under nitrogen. All other reagents and solvents were purchased as the highest grade available and used without further purification. Thin-layer chromatography (TLC) analysis of reaction mixtures was performed using Merck silica gel 60 F254 TLC plates and visualized using ultraviolet light. Silica gel 60 (40-63 μm, Merck) was used for flash chromatography. Melting points were measured using an Electrothermal 1002 apparatus and were uncorrected. $^1$H NMR (300 MHz) and $^{13}$C NMR (75 MHz) spectra were obtained on a Bruker Advance 300 NMR spectrometer using residual signal of deuterated NMR solvent as internal reference. Mass spectral data and purity of all compounds were acquired on an Agilent LCMS-Ion Trap-1200 Series. Mass spectra were obtained on an Agilent Ion Trap applying electrospray ionization (ESI). Purity of all compounds was obtained using a Nucleodur 3 μm 4.6×150 mm reverse-phase column. The eluent was a linear gradient with a flow rate of 1.3 mL/min from 95% A and 5% B to 5% A and 95% B in 8.5 min (solvent A, $H_2O$ with 0.1% $HCO_2H$; solvent B, acetonitrile with 0.1% $HCO_2H$). The compounds were detected at their maximum of absorbance.

In the examples below, in case the structures contain one or more stereogenic centers, the respective structure is depicted in an arbitrary absolute configuration. These structures also include the respective structure having the opposite stereochemistry and the corresponding racemate.

General Procedures
General Procedure a: Aldol Condensation to α,β-Unsaturated Esters A solution of the aldehyde (1.0 equiv.) and monoethyl malonate (1.3 equiv.) in anhydrous pyridine (5 equiv.) containing piperidine (0.1 equiv.) was refluxed for 12 h under an argon atmosphere. The reaction mixture was cooled to room temperature, quenched with 2N HCl, and extracted with ether. The extracts were washed with water, saturated $NaHCO_3$, and brine. The organic solution was dried over $Na_2SO_4$ and concentrated in vacuo. The crude mixture was purified by FC ($SiO_2$, cyclohexane/$CH_2Cl_2$) to furnish the pure α,β-unsaturated ester.

General Procedure B: Cyclopropanation of α,β-Unsaturated Esters

To a suspension of the alkylphosphonium iodide (1.0 equiv.) in anhydrous THF (0.3 M) at −78° C. was added n-BuLi (2.0 M in cyclohexane, 1.0 equiv.) under an argon atmosphere. The resulting mixture was warmed to 0° C. and stirred for 30 min. The reaction mixture was cooled to −78° C. followed by the addition of a solution of the α,β-unsaturated ester (1.0 equiv.) in anhydrous THF (0.5 M). The reaction mixture was stirred for 2 h at 0° C., then slowly warmed to 25° C., and stirred overnight. The solution was poured onto 1N HCl. The aqueous layer was extracted with EtOAc. The combined organic layers were sequentially washed with saturated $NaHCO_3$, brine, dried over $Na_2SO_4$, and concentrated in vacuo. The crude cyclopropane was purified by flash chromatography ($SiO_2$, cyclohexane/$CH_2Cl_2$) to furnish the pure cyclopropyl ester.

General Procedure C: Saponification of Esters

To the ester (1.0 equiv.) in solution in THF:water (1:4) (0.4 M), was added NaOH (1.1 equiv.). The mixture was stirred overnight at 60° C. and concentrated in vacuo. The aqueous layer was first extracted with $Et_2O$ and poured onto 1N HCl and then twice extracted with EtOAc. EtOAc extractions were combined and washed with brine, dried over $Na_2SO_4$ and concentrated in vacuo to furnish the pure carboxylic acid.

General Procedure D: Amide Bond Formation Through Acid Chloride Intermediates

To the carboxylic acid (1.0 equiv.) was added thionyl chloride (10.0 equiv.) at 0° C. and 2 drops of anhydrous DMF under an argon atmosphere. The mixture was stirred for 2 h at room temperature before the mixture was concentrated in vacuo. Co-evaporation with toluene, in vacuo, was used to remove the remaining thionyl chloride. The crude acid chloride was dissolved in anhydrous DCM under an argon atmosphere, cooled to 0° C. and $Et_3N$ (5.0 equiv.) was added followed by the addition of aniline/amine (1.0 equiv.). The mixture was stirred for 16 h at rt. The reaction mixture was directly purified by flash chromatography ($SiO_2$, cyclohexane/EtOAc) to furnish the pure amide.

General Procedure E: Formation of Sulfonamides

Chlorosulfonic acid (12-16 equiv.) was added drop-wise at 0° C. to a solution of the arene (1.0 equiv.) in chloroform (0.5 M) under an argon atmosphere. The reaction mixture was stirred at rt for 30 min, then poured into a water/ice/brine mixture. The phases were separated and the aqueous layer extracted with $Et_2O$ twice. The combined organic extracts were dried over $Na_2SO_4$, and concentrated in vacuo. The crude sulfonyl chloride was dissolved in a 0.5 M solution of ammonia in dioxane (10.0 equiv.), stirred at rt for 45 min and evaporated to dryness under vacuum overnight. The crude sulfonamide was taken up in 4N HCl in dioxane and concentrated in vacuo. The crude sulfonamide was purified by flash chromatography ($SiO_2$, cyclohexane/EtOAc then EtOAc/MeOH) or triturated with EtOAc/MeOH to give the pure sulfonamide.

General Procedure F: Amide Bond Formation Through EDCI/HOBt

To a solution of the carboxylic acid (1.0 equiv.) in anhydrous DCM (0.15-0.20 M) was added Et$_3$N (1.3-2.0 equiv.), the amine/aniline (1.0 equiv.), HOBt monohydrate (0.1 equiv.) at rt and then EDCI (1.3 equiv.) was added at 0° C. under an argon atmosphere. The mixture was stirred for 12 h at it before being concentrated in vacuo. The residue was dissolved in EtOAc and the organics were washed with 1N HCl, saturated NaHCO$_3$, brine, dried over Na$_2$SO$_4$, and concentrated in vacuo. The crude mixture was purified by flash chromatography (SiO$_2$, cyclohexane/AcOEt) to furnish the pure amide.

Ethyl 2,2-dimethyl-trans-3-phenylcyclopropanecarboxylate

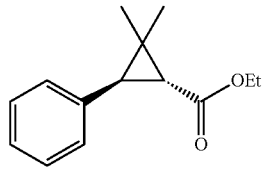 [SMILES: CCOC(=O)[C@@H]1[C@@H](c2ccccc2)C1(C)C]

Isopropyltriphenylphosphonium iodide (21.6 g, 50 mmol) and ethyl cinnamate (8.81 g, 50 mmol) were reacted as described under General Procedure B to furnish the title compound (6.58 g, 60%) as a colorless oil. $^1$H NMR (300 MHz, CDCl$_3$) δ 7.31-7.15 (m, 5H), 4.18 (q, J=7.3 Hz, 2H), 2.70 (d, J=5.6 Hz, 1H), 1.96 (d, J=5.6 Hz, 1H), 1.38 (s, 3H), 1.31 (t, J=7.3 Hz, 3H), 0.93 (s, 3H).

2,2-Dimethyl-trans-3-phenylcyclopropanecarboxylic acid

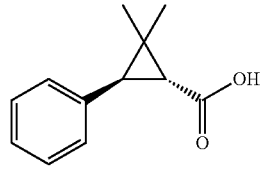

Ethyl 2,2-dimethyl-trans-3-phenylcyclopropanecarboxylate (6.58 g, 30.1 mmol) was reacted as described under General Procedure C to furnish the title compound (5.15 g, 90%) as a white solid. $^1$H NMR (300 MHz, CDCl$_3$) δ 7.33-7.17 (m, 5H), 2.77 (d, J=5.9 Hz, 1H), 1.99 (d, J=5.9 Hz, 1H), 1.45 (s, 3H), 0.96 (s, 3H).

Ethyl 4-chloro-cinnamate

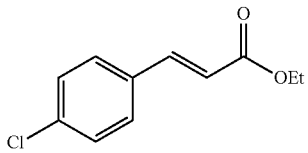 [SMILES: CCOC(=O)/C=C/c1ccc(Cl)cc1]

4-Chlorobenzaldehyde (4.20 g, 30 mmol) and mono-ethyl malonate (4.60 ml, 39 mmol) were reacted as described under General Procedure A to furnish the title compound (5.68 g, 89%) as a colorless oil. $^1$H NMR (300 MHz, CDCl$_3$) δ 7.63 (d, J=16.0 Hz, 1H), 7.46-7.42 (m, 2H), 7.38-7.32 (m, 2H), 6.41 (d, J=16.0 Hz, 1H), 4.26 (q, J=7.2 Hz, 2H), 1.33 (t, J=7.2 Hz, 3H).

Ethyl trans-3-(4-chlorophenol)-2,2-dimethylcyclopropanecarboxylate

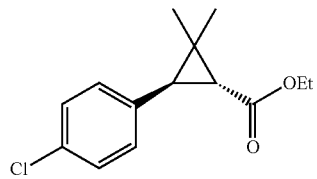 [SMILES: CCOC(=O)[C@@H]1[C@@H](c2ccc(Cl)cc2)C1(C)C]

Isopropyltriphenylphosphonium iodide (8.65 g, 20 mmol) and ethyl 4-chloro-cinnamate (4.21 g, 20 mmol) were reacted as described under General Procedure B to furnish the title compound (2.42 g, 48%) as a colorless oil. $^1$H NMR (300 MHz, CDCl$_3$) δ 7.26-7.24 (m, 2H), 7.11-7.08 (m, 2H), 4.18 (q, J=7.2 Hz, 2H), 2.63 (d, J=5.8 Hz, 1H), 1.91 (d, J=5.8 Hz, 1H), 1.42 (s, 3H), 1.30 (t, J=7.2 Hz, 3H), 0.91 (s, 3H). ESIMS m/z [M+H]$^+$ 253.1.

trans-(4-Chlorophenol)-2,2-dimethylcyclopropanecarboxylic acid

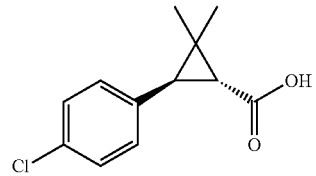

Ethyl trans-3-(4-chlorophenyl)-2,2-dimethylcyclopropanecarboxylate (2.42 g, 9.6 mmol) was reacted as described under General Procedure C to furnish the title compound (1.98 g, 92%) as a white solid. $^1$H NMR (300 MHz, CDCl$_3$) δ 7.28-7.25 (m, 2H), 7.12-7.09 (m, 2H), 2.70 (d, J=5.8 Hz, 1H), 1.93 (d, J=5.8 Hz, 1H), 1.42 (s, 3H), 0.94 (s, 3H).

Ethyl trans-2-phenylspiro[2.4]heptane-1-carboxylate

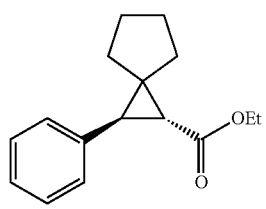 [SMILES: CCOC(=O)[C@@H]1[C@@H](c2ccccc2)C12CCCC2]

Cyclopentyltriphenylphosphonium bromide (10.3 g, 25 mmol) and ethyl cinnamate (4.40 g, 25 mmol) were reacted as described under General Procedure B to furnish the title compound (3.72 g, 61%) as a colorless oil. $^1$H NMR (300 MHz, CDCl$_3$) δ 7.32-7.11 (m, 5H), 4.22-4.13 (m, 2H), 2.77 (d, J=5.7 Hz, 1H), 2.15 (d, J=5.7 Hz, 1H), 1.91-1.85 (m, 2H), 1.72-1.27 (m, 9H).

trans 2-Phenylspiro[2.4]heptane-1-carboxylic acid

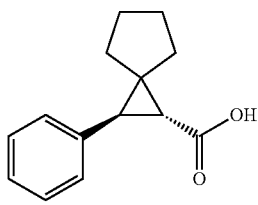 [SMILES: O=C(O)[C@@H]1[C@@H](c2ccccc2)C12CCCC2]

Ethyl trans-2-phenylspiro[2.4]heptane-1-carboxylate (3.72 g, 15.2 mmol) was reacted as described under General Procedure C to furnish the title compound (3.19 g, 96%) as a white solid. $^1$H NMR (300 MHz, CDCl$_3$) δ 7.33-7.11 (m, 5H), 2.83 (d, J=5.6 Hz, 1H), 2.17 (d, J=5.6 Hz, 1H), 1.97-1.32 (m, 8H).

Ethyl trans-2-phenylspiro[2.5]octane-1-carboxylate

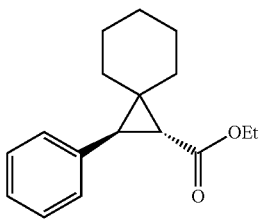 [SMILES: CCOC(=O)[C@@H]1[C@@H](c2ccccc2)C12CCCCC2]

Cyclohexyltriphenylphosphonium bromide (12.8 g, 30 mmol) and ethyl cinnamate (5.29 g, 30 mmol) were reacted as described under General Procedure B to furnish the title compound (0.30 g, 4%) as a colorless oil. $^1$H NMR (300 MHz, CDCl$_3$) δ 7.31-7.17 (m, 5H), 4.18 (q, J=7.0 Hz, 2H), 2.72 (d, J=5.9 Hz, 1H), 1.98 (d, J=5.9 Hz, 1H), 1.80-1.75 (m, 2H), 1.65-1.06 (m, 11H).

trans-2-Phenylspiro[2.5]octane-1-carboxylic acid

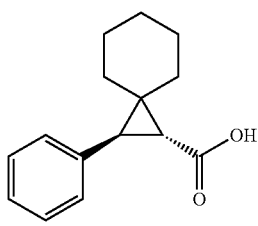 [SMILES: O=C(O)[C@@H]1[C@@H](c2ccccc2)C12CCCCC2]

Ethyl trans-2-phenylspiro[2.5]octane-1-carboxylate (300 mg, 1.16 mmol) was reacted as described under General Procedure C to furnish the title compound (224 mg, 83%) as a white solid. $^1$H NMR (300 MHz, CDCl$_3$) δ 7.32-7.19 (m, 5H), 2.78 (d, J=5.7 Hz, 1H), 2.00 (d, J=5.7 Hz, 1H), 1.82-1.07 (m, 10H).

Example 1a 2,2-Dimethyl-trans-N-(5-methylthiazol-2-yl)-3-phenylcyclopropanecarboxamide

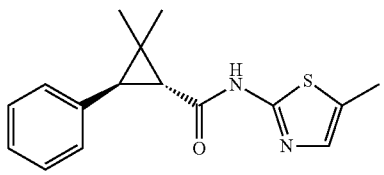 [SMILES: Cc1cnc(NC(=O)[C@@H]2[C@@H](c3ccccc3)C2(C)C)s1]

2,2-Dimethyl-trans-3-phenylcyclopropanecarboxylic acid (250 mg, 1.32 mmol) and 2-amino-5-methylthiazole (150 mg, 1.31 mmol) were reacted as described under General Procedure D to furnish the title compound (232 mg, 61%) as a yellow foam. $^1$H NMR (300 MHz, CDCl$_3$) δ 7.33-7.17 (m, 6H), 7.02 (s, 1H), 2.95 (d, J=5.6 Hz, 1H), 2.37 (s, 3H), 2.08 (d, J=5.6 Hz, 1H), 1.44 (s, 3H), 1.03 (s, 3H). mp 132-135° C. ESIMS m/z [M+H]$^+$ 287.1.

Example 1b (1R,3R)-2,2-dimethyl-N-(5-methylthiazol-2-yl)-3-(4-sulfamoylphenyl)cyclopropane carboxamide

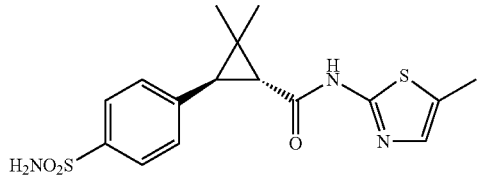 [SMILES: Cc1cnc(NC(=O)[C@@H]2[C@@H](c3ccc(S(N)(=O)=O)cc3)C2(C)C)s1]

Example 1a (138 mg, 0.48 mmol) was reacted as described under General Procedure E to give the title compound (147 mg, 84%) as a white foam. $^1$H NMR (300 MHz, d$_6$-DMSO) δ 12.15 (br s, 1H), 7.77 (d, J=8.3 Hz, 2H), 7.40 (d, J=8.3 Hz, 2H), 7.32 (br s, 2H), 7.13 (s, 1H), 2.71 (d, J=5.9 Hz, 1H), 2.43 (d, J=5.9 Hz, 1H), 2.33 (s, 3H), 1.32 (s, 3H), 0.88 (s, 3H). ESIMS m/z [M+H]$^+$ 366.1.

Example 2a 2,2-Dimethyl-trans-3-phenyl-N-(3-(trifluoromethyl)-1H-pyrazol-5-yl)cyclopropanecarboxamide

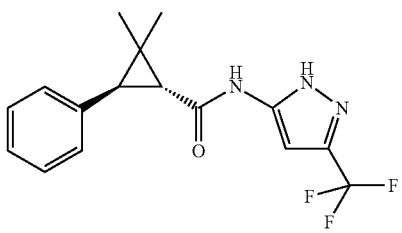 [SMILES: CC1(C)[C@H](C(=O)Nc2cc(C(F)(F)F)n[nH]2)[C@H]1c1ccccc1]

2,2-Dimethyl-trans-3-phenylcyclopropanecarboxylic acid (250 mg, 1.32 mmol) and 3-trifluoromethyl-1H-pyrazole-5-ylamine (198 mg, 1.31 mmol) were reacted as described under General Procedure D to furnish the title compound (392 mg, 93%) as a white solid. $^1$H NMR (300 MHz, CDCl$_3$) δ 7.32-7.22 (m, 6H), 5.72-5.64 (m, 2H), 3.43 (d, J=6.1 Hz, 1H), 2.98 (d, J=6.1 Hz, 1H), 1.42 (s, 3H), 1.07 (s, 3H). mp 68-71° C. ESIMS m/z [M+H]$^+$ 324.1.

Example 2b 2,2-Dimethyl-trans-3-(4-sulfamoylphenyl)-N-(3-(trifluoromethyl)-1H-pyrazol-5-yl)cyclopropanecarboxamide

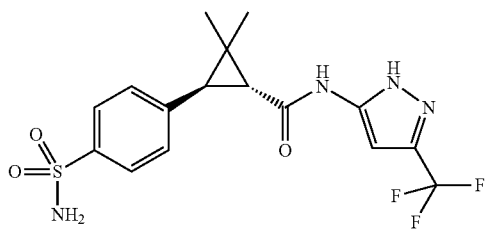 [SMILES: CC1(C)[C@H](C(=O)Nc2cc(C(F)(F)F)n[nH]2)[C@H]1c1ccc(S(N)(=O)=O)cc1]

Example 2a (260 mg, 0.80 mmol) was reacted as described under General Procedure E to give the title compound (103 mg, 32%) as a white foam. $^1$H NMR (300 MHz, d$_6$-DMSO) δ 13.48 (br s, 1H), 11.16 (bs, 1H), 7.77 (d, J=8.3 Hz, 2H), 7.41 (d, J=8.3 Hz, 2H), 7.34 (br s, 2H), 6.39 (br s, 1H), 2.69 (d, J=5.8 Hz, 1H), 2.31 (d, J=5.8 Hz, 1H), 1.33 (s, 3H), 0.89 (s, 3H). mp 210-213° C. ESIMS m/z [M+H]$^+$ 403.1.

Example 3a trans-N-(5-Chloro-2,4-dimethoxyphenyl)-2,2-dimethyl-3-phenylcyclopropanecarboxamide

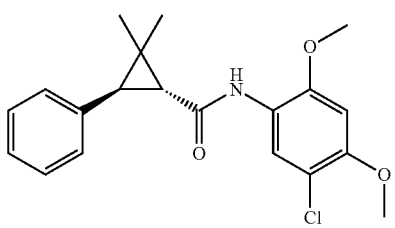 [SMILES: COc1cc(OC)c(NC(=O)[C@@H]2[C@@H](c3ccccc3)C2(C)C)cc1Cl]

2,2-Dimethyl-trans-3-phenylcyclopropanecarboxylic acid (500 mg, 2.63 mmol) and 5-chloro-2,4-dimethoxyaniline (493 mg, 2.63 mmol) were reacted as described under General Procedure D to furnish the title compound (620 mg, 66%) as a beige solid. $^1$H NMR (300 MHz, CDCl$_3$) δ 8.49 (s, 1H), 7.78 (s, 1H), 7.30-7.19 (m, 5H), 6.53 (s, 1H), 3.94 (s, 3H), 3.89 (s, 3H), 2.83 (d, J=5.7 Hz, 1H), 1.86 (d, J=5.7 Hz, 1H), 1.42 (s, 3H), 0.97 (s, 3H). mp 160-162° C. ESIMS m/z [M+H]$^+$ 360.2.

Example 3b trans-N-(5-Chloro-2,4-dimethoxyphenyl)-2,2-dimethyl-3-(4-sulfamoylphenyl)cyclopropanecarboxamide

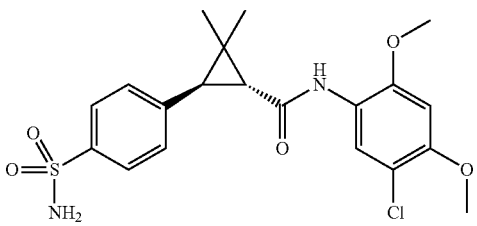 [SMILES: COc1cc(OC)c(NC(=O)[C@@H]2[C@@H](c3ccc(S(N)(=O)=O)cc3)C2(C)C)cc1Cl]

Example 3a (175 mg, 0.49 mmol) was reacted as described under General Procedure E to give the title compound (112 mg, 53%) as a white solid. $^1$H NMR (300 MHz, d$_6$-DMSO) δ, 9.44 (s, 1H), 8.09 (s, 1H), 7.77 (d, J=8.2 Hz, 2H), 7.41 (d, J=8.2 Hz, 2H), 7.33 (s, 2H), 6.86 (s, 1H), 3.94 (s, 3H), 3.87 (s, 3H), 2.66-2.62 (m, 2H), 1.33 (s, 3H), 0.87 (s, 3H). mp 248-251° C. ESIMS m/z [M+H]$^+$ 439.2.

Example 4a trans-N-(5-Chloro-2-methoxyphenyl)-2,2-dimethyl-3-phenylcyclopropanecarboxamide

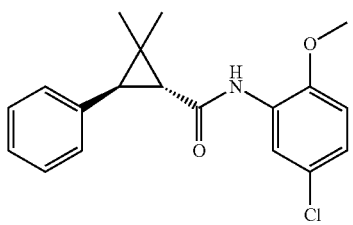 [SMILES: COc1ccc(Cl)cc1NC(=O)[C@@H]1[C@@H](c2ccccc2)C1(C)C]

2,2-Dimethyl-trans-3-phenylcyclopropanecarboxylic acid (1.90 mg, 10 mmol) and 4-chloro-2-methoxyaniline (1.58 mg, 10 mmol) were reacted as described under General Procedure F to furnish the title compound (490 mg, 15%) as a white solid. $^1$H NMR (300 MHz, CDCl$_3$) δ 8.52 (s, 1H), 7.98 (s, 1H), 7.32-7.19 (m, 5H), 6.98 (dd, J=8.7, 2.5 Hz, 1H), 6.79 (d, J=8.7 Hz, 1H), 3.92 (s, 3H), 2.85 (d, J=5.7 Hz, 1H), 1.88 (d, J=5.7 Hz, 1H), 1.42 (s, 3H), 0.99 (s, 3H). mp 155-157° C. ESIMS m/z [M+H]$^+$ 330.1.

Example 4b trans-N-(5-Chloro-2-methoxyphenyl)-2,2-dimethyl-3-(4-sulfamoylphenyl)cyclopropanecarboxamide

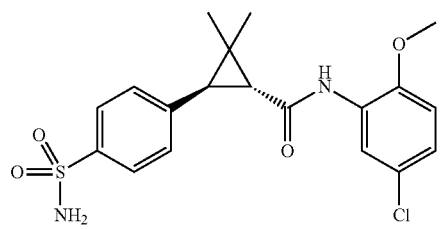 [SMILES: COc1ccc(Cl)cc1NC(=O)[C@@H]1[C@@H](c2ccc(S(N)(=O)=O)cc2)C1(C)C]

Example 4a (430 mg, 1.30 mmol) was reacted as described under General Procedure E to give the title compound (357 mg, 67%) as a white solid. $^1$H NMR (300 MHz, $d_5$-DMSO) δ 9.58 (s, 1H), 8.24 (s, 1H), 7.77 (d, J=8.3 Hz, 2H), 7.42 (d, J=8.3 Hz, 2H), 7.33 (s, 2H), 7.12-7.05 (m, 2H), 3.89 (s, 3H), 2.78 (d, J=5.9 Hz, 1H), 2.64 (d, J=5.9 Hz, 1H), 1.33 (s, 3H), 0.88 (s, 3H). mp 129-133° C. ESIMS m/z [M+H]$^+$ 409.1.

Example 5a trans-N-(5-Chloro-2-methoxyphenyl)-3-(4-chlorophenyl)-2,2-dimethylcyclopropanecarboxamide

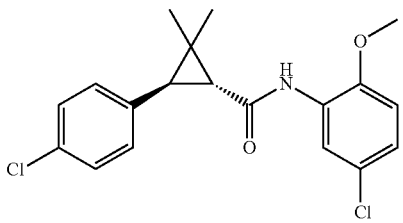 [SMILES: COc1ccc(Cl)cc1NC(=O)[C@@H]1[C@@H](c2ccc(Cl)cc2)C1(C)C]

trans-3-(4-Chlorophenyl)-2,2-dimethylcyclopropanecarboxylic acid (200 mg, 0.89 mmol) and 4-chloro-2-methoxyaniline (140 mg, 0.89 mmol) were reacted as described under General Procedure D to furnish the title compound (120 mg, 37%) as a white solid. $^1$H NMR (300 MHz, CDCl$_3$) δ 8.50 (d, J=2.5 Hz, 1H), 7.99 (br s, 1H), 7.27-7.24 (m, 2H), 7.13 (d, J=8.3 Hz, 2H), 6.99 (dd, J=8.7, 2.5 Hz, 1H), 6.79 (d, J=8.7 Hz, 1H), 3.92 (s, 3H), 2.80 (d, J=5.6 Hz, 1H), 1.84 (d, J=5.6 Hz, 1H), 1.40 (s, 3H), 0.97 (s, 3H). mp 162-164°. ESIMS m/z [M+H]$^+$ 364.1.

Example 6a trans-N-(5-Chloro-2-methoxyphenyl)-2-phenylspirol[2.4]heptane-1-carboxamide

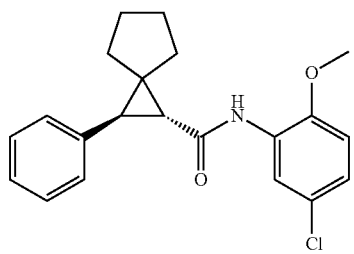 [SMILES: COc1ccc(Cl)cc1NC(=O)[C@@H]1[C@@H](c2ccccc2)C12CCCC2]

trans-2-Phenylspiro[2.4]heptane-1-carboxylic acid (400 mg, 1.85 mmol) and 4-chloro-2-methoxyaniline (291 mg, 1.85 mmol) were reacted as described under General Procedure D to furnish the title compound (560 mg, 85%) as a beige solid. $^1$H NMR (300 MHz, CDCl$_3$) δ 8.52 (d, J=2.5 Hz, 1H), 7.97 (br s, 1H), 7.33-7.14 (m, 5H), 6.99 (dd, J=8.7, 2.5 Hz, 1H), 6.79 (d, J=8.7 Hz, 1H), 3.91 (s, 3H), 2.90 (d, J=5.5 Hz, 1H), 2.05 (d, J=5.5 Hz, 1H), 1.96-1.91 (m, 2H), 1.71-1.42 (m, 6H). mp 133-135° C. ESIMS m/z [M+H]$^+$ 356.2.

Example 6b trans-N-(5-Chloro-2-methoxyphenyl)-2-(4-sulfamoylphenyl)spiro[2.4]heptane-1-carboxamide

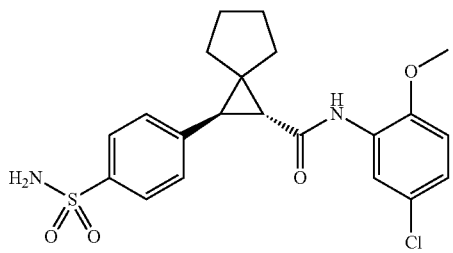 [SMILES: COc1ccc(Cl)cc1NC(=O)[C@@H]1[C@@H](c2ccc(S(N)(=O)=O)cc2)C12CCCC2]

Example 6a (200 mg, 0.56 mmol) was reacted as described under General Procedure E to give the title compound (140 mg, 58%) as a white solid. $^1$H NMR (300 MHz, $d_6$-DMSO) δ 9.53 (s, 1H), 8.22 (br s, 1H), 7.75 (d, J=8.3 Hz, 2H), 7.35 (d, J=8.3 Hz, 2H), 7.27 (s, 2H), 7.09-06 (m, 2H), 3.86 (s, 3H), 2.93 (d, J=5.5 Hz, 1H), 2.72 (d, J=5.5 Hz, 1H), 1.85-1.74 (m, 2H), 1.62-1.45 (m, 6H). mp 210-212° C. ESIMS m/z [M+H]$^+$ 435.2.

Example 7a trans-N-(5-Chloro-2-methoxyphenyl)-2-phenylspiro[2.5]octane-1-carboxamide

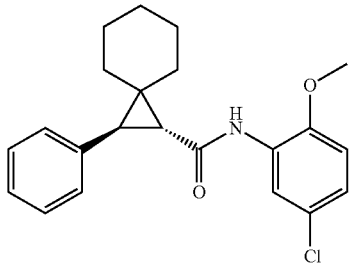 [SMILES: COc1ccc(Cl)cc1NC(=O)[C@@H]1[C@@H](c2ccccc2)C12CCCCC2]

trans-2-Phenylspiro[2.5]octane-1-carboxylic acid (220 mg, 0.95 mmol) and 4-chloro-2-methoxyaniline (150 mg, 0.95 mmol) were reacted as described under General Procedure D to furnish the title compound (270 mg, 77%) as a white foam. $^1$H NMR (300 MHz, CDCl$_3$) δ 8.49 (d, J=3.0 Hz, 1H), 8.00 (s, 1H), 7.32-7.20 (m, 5H), 6.99 (dd, J=8.4, 3.0 Hz, 1H), 6.79 (d, J=8.4 Hz, 1H), 3.92 (s, 3H), 2.87 (d, J=5.8 Hz, 1H), 1.91 (d, J=5.8 Hz, 1H), 1.85-1.81 (m, 2H), 1.66-1.16 (m, 8H). ESIMS m/z [M+H]$^+$ 370.2.

Example 7b trans-N-(5-Chloro-2-methoxyphenyl)-2-(4-sulfamoylphenyl)spiro[2.5]octane-1-carboxamide

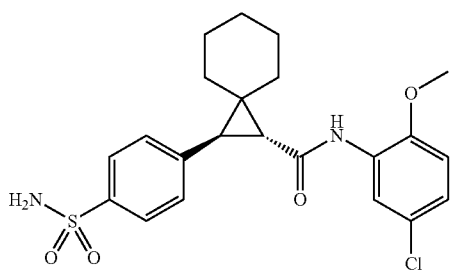 [SMILES: COc1ccc(Cl)cc1NC(=O)[C@@H]1[C@@H](c2ccc(S(N)(=O)=O)cc2)C12CCCCC2]

Example 7a (150 mg, 0.40 mmol) was reacted as described under General Procedure E to give the title compound (125 mg, 70%) as a white solid. $^1$H NMR (300 MHz, d$_3$-MeOD) δ 8.11 (d, J=2.4 Hz, 1H), 7.84 (d, J=8.4 Hz, 2H), 7.44 (d, J=8.4 Hz, 2H), 7.09-6.98 (m, 2H), 3.93 (s, 3H), 2.81 (d, J=5.6 Hz, 1H), 2.56 (d, J=5.6 Hz, 1H), 1.84-1.80 (m, 2H), 1.67-1.21 (m, 8H). mp 118-121° C. ESIMS m/z [M+H]$^+$ 449.2.

Example 8a trans-N-(2,6-dimethoxypyridin-3-yl)-2-phenylspiro[2.4]heptane-1-carboxamide

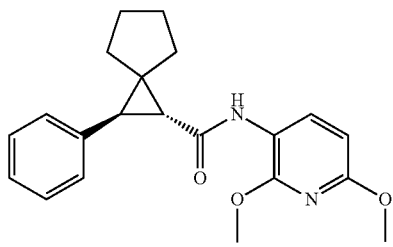 [SMILES: COc1ccc(NC(=O)[C@@H]2[C@@H](c3ccccc3)C23CCCC3)c(OC)n1]

trans-2-Phenylspiro[2.4]heptane-1-carboxylic acid (300 mg, 1.39 mmol) and 2,6-dimethoxy-pyridin-3-ylamine (214 mg, 1.39 mmol) were reacted as described under General Procedure D to furnish the title compound (260 mg, 52%) as a purple solid. $^1$H NMR (300 MHz, CDCl$_3$) δ 8.54 (d, J=8.2 Hz, 1H), 7.61 (br s, 1H), 7.32-7.14 (m, 5H), 6.30 (d, J=8.2 Hz, 1H), 4.02 (s, 3H), 3.89 (s, 3H), 2.87 (d, J=5.7 Hz, 1H), 2.05 (d, J=5.7 Hz, 1H), 1.93-1.90 (m, 2H), 1.67-1.42 (m, 6H). mp 131-133° C. ESIMS m/z [M+H]$^+$ 353.2.

Example 8b trans-N-(2,6-Dimethoxypyridin-3-yl)-2-(4-sulfamoylphenyl)spiro[2.4]heptane-1-carboxamide

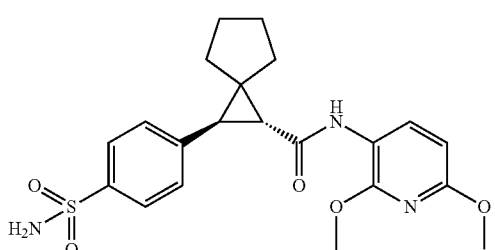

Example 8a (170 mg, 0.47 mmol) was reacted as described under General Procedure E to give the title compound (105 mg, 63%) as a white solid. $^1$H NMR (300 MHz, CDCl$_3$) δ 8.49 (d, J=8.5 Hz, 1H), 7.84 (d, J=8.4 Hz, 2H), 7.67 (br s, 1H), 7.27 (d, J=8.4 Hz, 2H), 6.30 (d, J=8.5 Hz, 1H), 4.91 (s, 2H), 4.02 (s, 3H), 3.89 (s, 3H), 2.93 (d, J=5.5 Hz, 1H), 2.14 (d, J=5.5 Hz, 1H), 1.94-1.90 (m, 2H), 1.75-1.31 (m, 6H). mp 112-115° C. ESIMS m/z [M+H]$^+$ 432.3.

Example 9a trans-2-phenyl-N-(4-(trifluoromethyl)phenyl)spiro[2.4]heptane-1-carboxamide

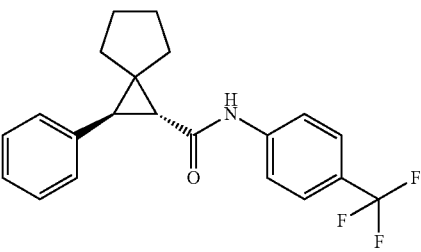 [SMILES: O=C(Nc1ccc(C(F)(F)F)cc1)[C@@H]1[C@@H](c2ccccc2)C12CCCC2]

trans-2-Phenylspiro[2.4]heptane-1-carboxylic acid (300 mg, 1.39 mmol) and 4-trifluoromethyl-phenylamine (224 mg, 1.39 mmol) were reacted as described under General Procedure D to furnish the title compound (300 mg, 60%) as a white solid. $^1$H NMR (300 MHz, CDCl$_3$) δ 7.69 (d, J=8.8 Hz, 2H), 7.58-7.52 (m, 3H), 7.33-7.20 (m, 3H), 7.15-7.12 (m, 2H), 2.92 (d, J=5.5 Hz, 1H), 2.06 (d, J=5.5 Hz, 1H), 1.93-1.91 (m, 2H), 1.73-1.60 (m, 4H), 1.52-1.40 (m, 2H). mp 171-173° C. ESIMS m/z [M+H]$^+$ 360.2.

Example 9b trans-2-(4-sulfamoylphenyl)-N-(4-(trifluoromethyl)phenyl)spiro[2.4]heptane-1-carboxamide

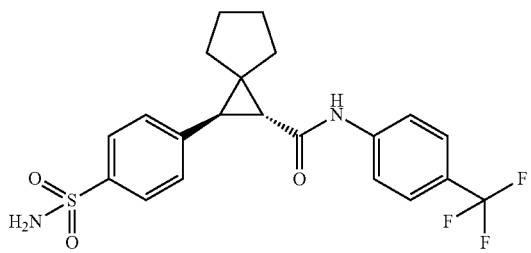 [SMILES: NS(=O)(=O)c1ccc([C@@H]2[C@@H](C(=O)Nc3ccc(C(F)(F)F)cc3)C23CCCC3)cc1]

Example 9a (190 mg, 0.47 mmol) was reacted as described under General Procedure E to give the title compound (145 mg, 63%) as a white solid. $^1$H NMR (300 MHz, d$_6$-DMSO) δ 10.57 (s, 1H), 7.83-7.75 (m, 4H), 7.65 (d, J=8.7 Hz, 2H), 7.35 (d, J=8.3 Hz, 2H), 7.29 (br s, 1H), 4.00 (S, 1H), 2.78 (d, J=5.7 Hz, 1H), 2.48 (d, J=5.7 Hz, 1H), 1.90-1.72 (m, 2H), 1.68-1.41 (m, 5H), 1.26-1.15 (m, 1H). mp 234-236° C. ESIMS m/z [M+H]$^+$ 439.2.

Example 10a 2,2-Dimethyl-trans-3-phenyl-N-(pyridin-4-yl)cyclopropanecarboxamide

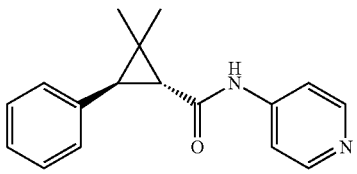 [SMILES: CC1(C)[C@H](C(=O)Nc2ccncc2)[C@H]1c1ccccc1]

2,2-Dimethyl-trans-3-phenylcyclopropanecarboxylic acid (250 mg, 1.31 mmol) and 4-aminopyridine (123 mg, 1.31 mmol) were reacted as described under General Procedure D to furnish the title compound (326 mg, 93%) as a white foam. $^1$H NMR (300 MHz, CDCl$_3$) δ 8.48-8.45 (m, 2H), 8.35 (br s, 1H), 7.63-7.60 (m, 2H), 7.31-7.16 (m, 5H), 2.87 (d, J=5.7 Hz, 1H), 1.96 (d, J=5.7 Hz, 1H), 1.40 (s, 3H), 0.97 (s, 3H). ESIMS m/z [M+H]$^+$ 267.1.

Example 10b 2,2-Dimethyl-trans-N-(pyridin-4-yl)-3-(4-sulfamoylphenyl)cyclopropanecarboxamide

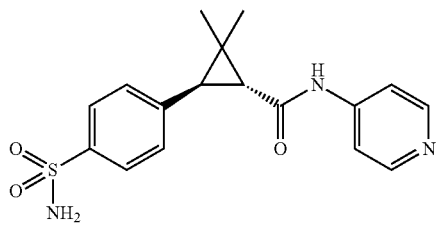 [SMILES: CC1(C)[C@H](C(=O)Nc2ccncc2)[C@H]1c1ccc(S(N)(=O)=O)cc1]

Example 10a (230 mg, 0.86 mmol) was reacted as described under General Procedure E to give the title compound (80 mg, 27%) as a white solid. $^1$H NMR (300 MHz, d$_6$-DMSO) δ 10.64 (br s, 1H), 8.43-8.41 (m, 2H), 7.77 (d, J=8.3 Hz, 2H), 7.60-7.57 (m, 2H), 7.42 (d, J=8.3 Hz, 2H), 7.34 (br s, 2H), 2.69 (d, J=5.9 Hz, 1H), 2.31 (d, J=5.9 Hz, 1H), 1.33 (s, 3H), 0.90 (s, 3H). mp 270-274° C. ESIMS m/z [M+H]$^+$ 346.2.

Example 11a trans-3-[4-(dimethylsulfamoyl)phenyl]-2,2-dimethyl) cyclopropanecarboxylic acid

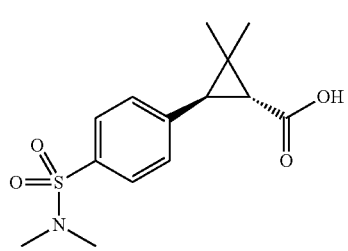 [SMILES: CN(C)S(=O)(=O)c1ccc([C@@H]2[C@@H](C(=O)O)C2(C)C)cc1]

2,2-Dimethyl-trans-3-phenylcyclopropanecarboxylic acid (4.0 g, 21.0 mmol) was reacted as described under General Procedure E using dimethylamine in THF (instead of ammonia in dioxane) to furnish the title compound (1.4 g, 95%) as a white solid. $^1$H NMR (300 MHz, d$_4$-methanol) δ 7.72 (d, J=8.1 Hz, 2H), 7.45 (d, J=8.1 Hz, 2H), 2.69-2.66 (m, 7H), 2.12 (d, J=6.0 Hz, 1H), 1.40 (s, 3H), 0.94 (s, 3H).

Example 11b trans-N-(5-Chloro-2-methoxyphenyl)-3-[4-(dimethylsulfamoyl)phenyl]-2,2-dimethylcyclopropanecarboxamide

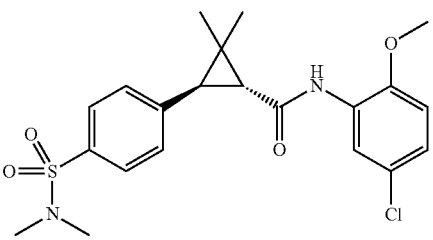 [SMILES: COc1ccc(Cl)cc1NC(=O)[C@@H]1[C@@H](c2ccc(S(=O)(=O)N(C)C)cc2)C1(C)C]

Example 11a (300 mg, 1.0 mmol) and 4-chloro-2-methoxyaniline (159 mg, 1.0 mmol) were reacted as described under General Procedure F to furnish the title compound (342 mg, 79%) as a white solid. $^1$H NMR (300 MHz, CDCl$_3$) δ 8.49 (brs, 1H), 8.03 (brs, 1H), 7.69 (d, J=8.3 Hz, 2H), 7.36 (d, J=8.3 Hz, 2H), 7.02-6.98 (m, 1H), 6.80 (d, J=8.7 Hz, 1H), 3.92 (s, 3H), 2.88 (d, J=5.5 Hz, 1H), 2.70 (s, 6H), 1.98 (d, J=5.5 Hz, 1H), 1.42 (s, 3H), 0.97 (s, 3H). ESIMS m/z [M+H]$^+$ 437.1.

Example 12a

Ethyl trans-3-(4-bromophenyl)-2,2-dimethylcyclopropanecarboxylate

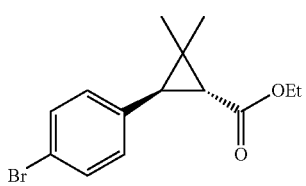 [SMILES: CCOC(=O)[C@@H]1[C@@H](c2ccc(Br)cc2)C1(C)C]

Isopropyltriphenylphosphonium iodide (8.65 g, 20.0 mmol) and ethyl 4-bromo-cinnamate (5.10 g, 20.0 mmol) were reacted as described under General Procedure B to furnish the title compound (3.21 g, 54%) as a colourless oil. $^1$H NMR (300 MHz, CDCl$_3$) δ 7.40 (d, J=8.3 Hz, 2H), 7.03 (d, J=8.3 Hz, 2H), 4.18 (q, J=7.1 Hz, 2H), 2.62 (d, J=5.5 Hz, 1H), 1.91 (d, J=5.5 Hz, 1H), 1.36 (s, 3H), 1.30 (t, J=7.1 Hz, 3H), 0.91 (s, 3H).

Example 12b trans-3-(4-bromophenyl)-2,2-dimethylcyclopropanecarboxylic acid

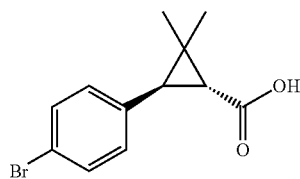

Ethyl trans-3-(4-bromophenyl)-2,2-dimethylcyclopropanecarboxylate (3.21 g, 10.8 mmol) was reacted as described under General Procedure C to furnish the title compound (2.57 g, 88%) as a white solid. ¹H NMR (300 MHz, CDCl₃) δ 7.40 (d, J=7.9 Hz, 2H), 7.05 (d, J=7.9 Hz, 2H), 2.68 (d, J=5.8 Hz, 1H), 1.93 (d, J=5.8 Hz, 1H), 1.42 (s, 3H), 0.94 (s, 3H).

Example 12c trans-N-(5-Chloro-2-methoxyphenyl)-3-(4-bromophenyl)-2,2-dimethylcyclopropanecarboxamide

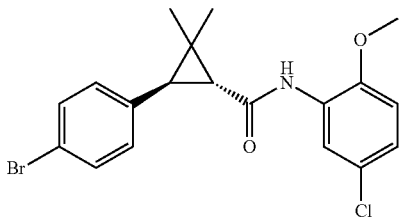

trans-3-(4-Bromophenyl)-2,2-dimethylcyclopropanecarboxylic acid (200 mg, 0.74 mmol) and 4-chloro-2-methoxyaniline (120 mg, 0.74 mmol) were reacted as described under General Procedure D to furnish the title compound (270 mg, 89%) as a white solid. ¹H NMR (300 MHz, CDCl₃) δ 8.50 (brs, 1H), 7.98 (brs, 1H), 7.41 (d, J=8.1 Hz, 2H), 7.08 (d, J=8.1 Hz, 2H), 6.99 (dd, J=8.7, 2.5 Hz, 1H), 6.80 (d, J=8.7 Hz, 1H), 3.91 (s, 3H), 2.78 (d, J=5.6 Hz, 1H), 1.83 (d, J=5.6 Hz, 1H), 1.39 (s, 3H), 0.97 (s, 3H). mp 170-172°. ESIMS m/z [M+H]⁺ 410.1.

Example 13a trans-N-(2-methoxypyridin-3-yl)-2,2-dimethyl-3-phenylcyclopropanecarboxamide

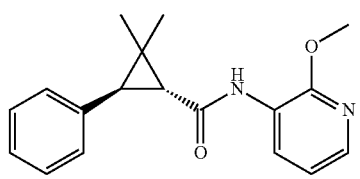 [SMILES: COc1ncccc1NC(=O)[C@@H]1[C@@H](c2ccccc2)C1(C)C]

2,2-Dimethyl-trans-3-phenylcyclopropanecarboxylic acid (400 mg, 2.1 mmol) and 2-methoxy-3-pyridinamine (261 mg, 2.1 mmol) were reacted as described under General Procedure D to furnish the title compound (550 mg, 88%) as a white solid. ¹H NMR (300 MHz, CDCl₃) δ 8.69-8.64 (m, 1H), 7.90 (s, 1H), 7.85-7.83 (m, 1H), 7.32-7.19 (m, 5H), 6.92-6.88 (m, 1H), 4.06 (s, 3H), 2.84 (d, J=5.7 Hz, 1H), 1.90 (d, J=5.7 Hz, 1H), 1.41 (s, 3H), 0.98 (s, 3H). mp 152-154° C. ESIMS m/z [M+H]⁺ 297.2.

Example 13b trans-N-(2-methoxypyridin-3-yl)-2,2-dimethyl-3-(4-sulfamoylphenyl)cyclopropanecarboxamide

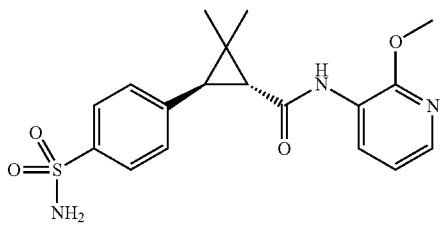 [SMILES: COc1ncccc1NC(=O)[C@@H]1[C@@H](c2ccc(S(N)(=O)=O)cc2)C1(C)C]

Example 13a (200 mg, 0.67 mmol) was reacted as described under General Procedure E to give the title compound (95 mg, 38%) as a white solid. ¹H NMR (300 MHz, CDCl₃/d₄-methanol) δ 8.40 (d, J=7.8 Hz, 1H), 7.71-7.68 (m, 3H), 7.21 (d, J=8.3 Hz, 2H), 6.78 (dd, J=7.8, 5.1 Hz, 1H), 3.91 (s, 3H), 2.69 (d, J=5.8 Hz, 1H), 2.02 (d, J=5.8 Hz, 1H), 1.27 (s, 3H), 0.83 (s, 3H). mp 216-218° C. ESIMS m/z [M+H]⁺ 376.2.

Example 14a

Ethyl 2,2-diethyl-trans-3-phenylcyclopropanecarboxylate

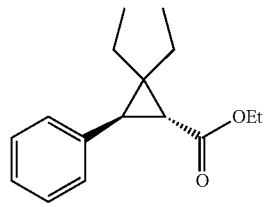 [SMILES: CCOC(=O)[C@@H]1[C@@H](c2ccccc2)C1(CC)CC]

3-Pentyltriphenylphosphonium bromide (8.27 g, 20 mmol) and ethyl cinnamate (3.52 g, 20.0 mmol) were reacted as described under General Procedure B to furnish the title compound (460 mg, 9%) as a colorless oil containing 14% of an isomeric impurity. ¹H NMR (300 MHz, CDCl₃) δ 7.33-7.12 (m, 5H), 4.16 (q, J=7.1 Hz, 2H), 2.70 (d, J=5.8 Hz, 1H), 1.94 (d, J=5.8 Hz, 1H), 1.77-1.22 (m, 7H), 0.98-0.80 (m, 6H).

Example 14b 2,2-Diethyl-trans-3-phenylcyclopropanecarboxylic acid

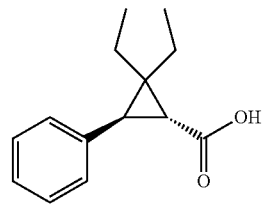 [SMILES: CCC1(CC)[C@H](C(=O)O)[C@H]1c1ccccc1]

Ethyl 2,2-diethyl-trans-3-phenylcyclopropanecarboxylate (460 g, 1.9 mmol) was reacted as described under General Procedure C to furnish the title compound (353 mg, 86%) as a white solid containing 25% of an isomeric impurity. $^1$H NMR (300 MHz, CDCl$_3$) δ 7.35-7.11 (m, 5H), 2.75 (d, J=5.8 Hz, 1H), 1.97 (d, J=5.8 Hz, 1H), 1.81-1.19 (m, 4H), 1.02-0.81 (m, 6H).

Example 14c trans-N-(5-Chloro-2-methoxyphenyl)-2,2-diethyl-3-phenylcyclopropanecarboxamide

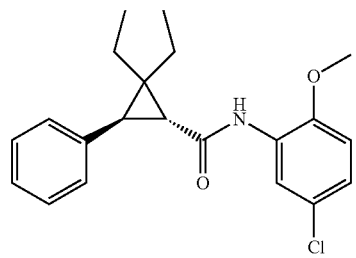 [SMILES: CCC1(CC)[C@H](C(=O)Nc2cc(Cl)ccc2OC)[C@H]1c1ccccc1]

2,2-Dimethyl-trans-3-phenylcyclopropanecarboxylic acid (350 mg, 1.6 mmol) and 4-chloro-2-methoxyaniline (253 mg, 1.6 mmol) were reacted as described under General Procedure F to furnish the title compound (430 mg, 75%) as a yellow oil containing 30% of an isomeric impurity. $^1$H NMR (300 MHz, CDCl$_3$) δ 8.50 (brs, 1H), 8.01 (brs, 1H), 7.32-7.19 (m, 5H), 7.00-6.96 (m, 1H), 6.79 (d, J=8.7 Hz, 1H), 3.90 (s, 3H), 2.85 (d, J=5.8 Hz, 1H), 1.87 (d, J=5.8 Hz, 1H), 1.80-1.21 (m, 4H), 1.00-0.82 (m, 6H).

ESIMS m/z [M+H]$^+$ 358.2.

Example 14d trans-N-(5-Chloro-2-methoxyphenyl)-2,2-diethyl-3-(4-sulfamoylphenyl)cyclopropanecarboxamide

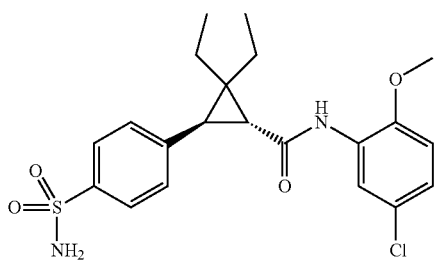 [SMILES: CCC1(CC)[C@H](C(=O)Nc2cc(Cl)ccc2OC)[C@H]1c1ccc(S(N)(=O)=O)cc1]

Example 14c (250 mg, 0.70 mmol) was reacted as described under General Procedure E to give the title compound (150 mg, 49%) as a white solid containing 28% of an isomeric impurity. $^1$H NMR (300 MHz, CDCl$_3$) δ 8.47 (brs, 1H), 8.00 (brs, 1H), 7.84 (d, J=8.3 Hz, 2H), 7.34 (d, J=8.3 Hz, 2H), 7.02-6.98 (m, 1H), 6.81 (d, J=8.7 Hz, 1H), 4.79 (s, 2H), 3.92 (s, 3H), 2.89 (d, J=5.8 Hz, 1H), 1.94 (d, J=5.8 Hz, 1H), 1.76-1.20 (m, 4H), 1.00-0.86 (m, 6H). ESIMS m/z [M+H]$^+$ 437.2.

Example 15a trans-2-phenyl-N-[2-chloro-4-(trifluoromethyl)phenyl]spiro[2.4]heptane-1-carboxamide

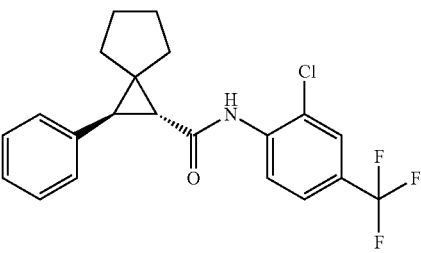 [SMILES: O=C(Nc1ccc(C(F)(F)F)cc1Cl)[C@@H]1[C@@H](c2ccccc2)C12CCCC2]

trans-2-Phenylspiro[2.4]heptane-1-carboxylic acid (300 mg, 1.39 mmol) and 2-chloro-4-trifluoromethyl-phenylamine (272 mg, 1.39 mmol) were reacted as described under General Procedure D to furnish the title compound (312 mg, 57%) as a white solid. $^1$H NMR (300 MHz, d$_6$-DMSO) δ 9.91 (s, 1H), 8.20 (d, J=8.5 Hz, 1H), 7.89 (d, J=1.6 Hz, 1H), 7.67 (d, J=8.5, 1.6 Hz, 1H), 7.31 (t, J=7.3 Hz, 2H), 7.22-7.16 (m, 3H), 2.80 (d, J=5.7 Hz, 1H), 2.70 (d, J=5.7 Hz, 1H), 1.82-1.73 (m, 2H), 1.66-1.42 (m, 5H), 1.29-1.10 (m, 1H). mp 131-133° C. ESIMS m/z [M+H]$^+$ 394.3.

Example 15b trans-2-(4-sulfamoylphenyl)-N-[2-chloro-4-(trifluoromethyl)phenyl]spiro[2.4]heptane-1-carboxamide

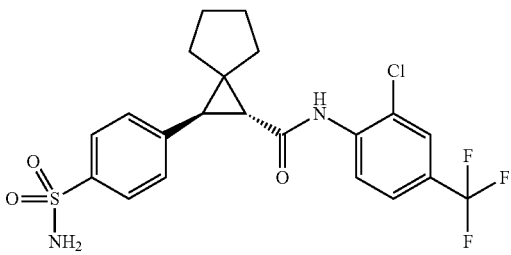 [SMILES: NS(=O)(=O)c1ccc([C@@H]2[C@@H](C(=O)Nc3ccc(C(F)(F)F)cc3Cl)C23CCCC3)cc1]

Example 15a (200 mg, 0.5 mmol) was reacted as described under General Procedure E to give the title compound (144 mg, 61%) as a white solid. $^1$H NMR (300 MHz, CDCl$_3$) δ 8.62 (d, J=8.5 Hz, 1H), 7.99 (s, 1H), 7.88 (d, J=8.5 Hz, 2H), 7.67 (s, 1H), 7.54 (d, J=8.5 Hz, 1H), 7.31 (d, J=8.5 Hz, 2H), 4.75 (s, 2H), 3.00 (d, J=5.4 Hz, 1H), 2.18 (d, J=5.4 Hz, 1H), 1.98-1.80 (m, 2H), 1.77-1.59 (m, 5H), 1.44-1.31 (m, 1H). mp 111-113° C. ESIMS m/z [M+H]$^+$ 473.3.

Example 16a

Ethyl 3-methyl-cinnamate

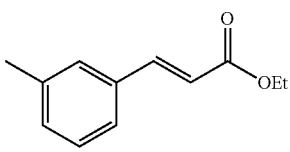

3-Methylbenzaldehyde (12.0 g, 100 mmol) and monoethyl malonate (15.5 ml, 130 mmol) were reacted as described under General Procedure A to furnish the title compound (16.7 g, 88%) as a yellow oil. $^1$H NMR (300 MHz, CDCl$_3$) δ 7.66 (d, J=16.0 Hz, 1H), 7.34-7.18 (m, 4H), 6.42 (d, J=16.0 Hz, 1H), 4.26 (q, J=7.2 Hz, 2H), 2.37 (s, 3H), 1.33 (t, J=7.2 Hz, 3H).

Example 16b

Ethyl trans-2,2-dimethyl-3-m-tolyl-cyclopropanecarboxylate

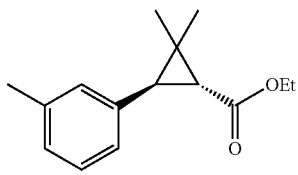 [SMILES: CCOC(=O)[C@@H]1[C@@H](c2cccc(C)c2)C1(C)C]

Isopropyltriphenylphosphonium iodide (17.3 g, 40 mmol) and ethyl 3-methylcinnamate (7.6 g, 40 mmol) were reacted as described under General Procedure B to furnish the title compound (7.0 g, 75%) as a colorless oil. $^1$H NMR (300 MHz, CDCl$_3$) δ 7.17 (t, J=7.4 Hz, 1H), 7.03-6.95 (m, 3H), 4.18 (q, J=7.2 Hz, 2H), 2.66 (d, J=5.8 Hz, 1H), 2.33 (s, 3H), 1.93 (d, J=5.8 Hz, 1H), 1.38 (s, 3H), 1.30 (t, J=7.2 Hz, 3H), 0.93 (s, 3H).

Example 16c trans-2,2-Dimethyl-3-m-tolyl-cyclopropanecarboxylic acid

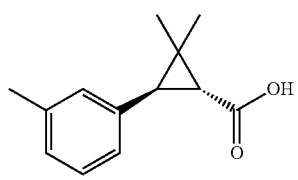

Ethyl trans-2,2-dimethyl-3-m-tolyl-cyclopropanecarboxylate (7.0 g, 30 mmol) was reacted as described under General Procedure C to furnish the title compound (5.4 g, 89%) as a yellow oil. $^1$H NMR (300 MHz, CDCl$_3$) δ 7.18 (t, J=7.4 Hz, 1H), 7.05-6.95 (m, 3H), 2.72 (d, J=5.8 Hz, 1H), 2.33 (s, 3H), 1.96 (d, J=5.8 Hz, 1H), 1.43 (s, 3H), 0.96 (s, 3H).

Example 16d trans-N-(3,4-Difluoro-phenyl)-2,2-dimethyl-3-m-tolyl-cyclopropanecarboxamide

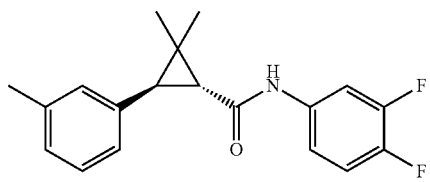 [SMILES: Cc1cccc([C@@H]2[C@@H](C(=O)Nc3ccc(F)c(F)c3)C2(C)C)c1]

trans-2,2-Dimethyl-3-m-tolyl-cyclopropanecarboxylic acid (2.04 g, 10 mmol) and 3,4-difluoroaniline (1.29 g, 10 mmol) were reacted as described under General Procedure D to furnish the title compound (2.9 g, 92%) as a brown solid. $^1$H NMR (300 MHz, CDCl$_3$) δ 7.70-7.64 (m, 1H), 7.47 (s, 1H), 7.20-6.96 (m, 6H), 2.79 (d, J=5.6 Hz, 1H), 2.33 (s, 3H), 1.80 (d, J=5.6 Hz, 1H), 1.40 (s, 3H), 0.97 (s, 3H). mp 110-113° C. ESIMS m/z [M+H]$^+$ 316.2.

Example 16e trans-N-(3,4-Difluoro-phenyl)-2,2-dimethyl-3-(3-methyl-4-sulfamoyl-phenyl)-cyclopropane carboxamide

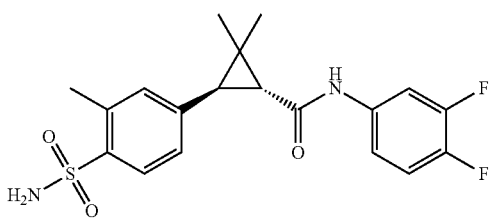 [SMILES: Cc1cc([C@@H]2[C@@H](C(=O)Nc3ccc(F)c(F)c3)C2(C)C)ccc1S(N)(=O)=O]

Example 16d (93 mg, 0.30 mmol) was reacted as described under General Procedure E to give the title compound (5.1 mg, 11%) as a white solid. $^1$H NMR (300 MHz, CD$_3$OD) δ 7.89 (d, J=8.1 Hz, 1H), 7.76-7.69 (m, 1H), 7.28-7.16 (m, 4H), 2.73 (d, J=6.0 Hz, 1H), 2.65 (s, 3H), 2.19 (d, J=6.0 Hz, 1H), 1.38 (s, 3H), 0.96 (s, 3H). mp 195-198° C. ESIMS m/z [M+H]$^+$ 395.3.

Example 17a trans-N-(5-Chloro-2-methoxyphenyl)-2,2-dimethyl-3-m-tolyl-cyclopropanecarboxamide

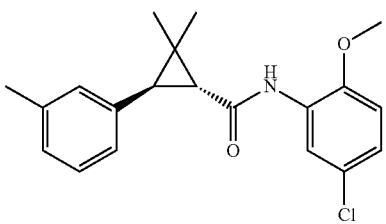

trans-2,2-Dimethyl-3-m-tolyl-cyclopropanecarboxylic acid (2.04 g, 10 mmol) and 4-chloro-2-methoxyaniline (2.73 g, 13.4 mmol) were reacted as described under General Procedure D to furnish the title compound (3.9 g, 85%) as a white solid. $^1$H NMR (300 MHz, CDCl$_3$) δ 8.52 (s, 1H), 7.99 (s, 1H), 7.18 (t, J=7.7 Hz, 1H), 7.04-6.96 (m, 4H), 6.86-6.69 (m, 1H), 3.92 (s, 3H), 2.80 (d, J=5.5 Hz, 1H), 2.34 (s, 3H), 1.86 (d, J=5.5 Hz, 1H), 1.40 (s, 3H), 0.98 (s, 3H). mp 148-150° C. ESIMS m/z [M+H]$^+$ 344.3.

Example 17b trans-N-(5-Chloro-2-methoxyphenyl)-2,2-dimethyl-3-(3-methyl-4-sulfamoyl-phenyl)-cyclopropane carboxamide

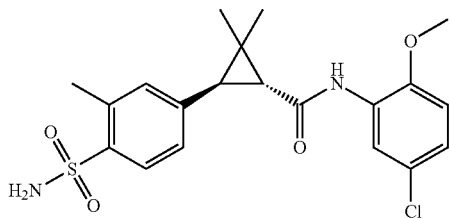 [SMILES: COc1ccc(Cl)cc1NC(=O)[C@@H]1[C@@H](c2ccc(S(N)(=O)=O)c(C)c2)C1(C)C]

Example 17a (131 mg, 0.38 mmol) was reacted as described under General Procedure E to give the title compound (4.1 mg, 3%) as a beige solid. $^1$H NMR (300 MHz, CDCl$_3$) δ 8.49 (s, 1H), 8.00 (s, 1H), 7.93 (d, J=8.1 Hz, 1H), 7.17-7.12 (m, 2H), 7.00 (d, J=8.6 Hz, 1H), 6.80 (d, J=8.6 Hz, 1H), 4.74 (s, 2H), 3.92 (s, 3H), 2.84 (d, J=5.8 Hz, 1H), 2.67 (s, 3H), 1.93 (d, J=5.8 Hz, 1H), 1.42 (s, 3H), 0.98 (s, 3H). mp 118-121° C. ESIMS m/z [M+H]$^+$ 423.4.

Example 18a

Ethyl 3-(2,2-difluoro-benzo[1,3]dioxol-5-yl)-acrylate

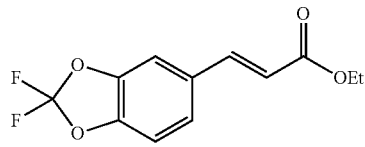 [SMILES: CCOC(=O)/C=C/c1ccc2c(c1)OC(F)(F)O2]

2,2-difluoro-1,3-benzodioxole-5-carboxaldehyde (5.0 g, 26.9 mmol) and mono-ethyl malonate (4.1 ml, 34.9 mmol) were reacted as described under General Procedure A to furnish the title compound (5.6 g, 82%) as a white solid. $^1$H NMR (300 MHz, CDCl$_3$) δ 7.61 (d, J=16.0 Hz, 1H), 7.26-7.22 (m, 2H), 7.06 (d, J=7.9 Hz, 1H), 6.33 (d, J=16.0 Hz, 1H), 4.26 (q, J=7.1 Hz, 2H), 1.33 (t, J=7.1 Hz, 3H).

Example 18b

Ethyl trans-3-(2,2-difluoro-benzo[1,3]dioxol-5-yl)-2,2-dimethylcyclopropanecarboxylate

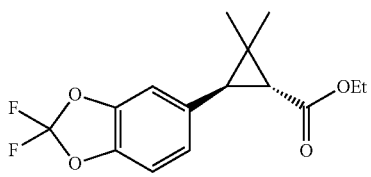

Isopropyltriphenylphosphonium iodide (4.32 g, 10 mmol) and ethyl 3-(2,2-difluoro-benzo[1,3]dioxol-5-yl)-acrylate (2.56 g, 10 mmol) were reacted as described under General Procedure B to furnish the title compound (1.62 g, 54%) as a colorless oil. $^1$H NMR (300 MHz, CDCl$_3$) δ 6.96 (d, J=7.1 Hz, 1H), 6.89 (s, 1H), 6.87 (d, J=7.1 Hz, 1H), 4.18 (q, J=7.2 Hz, 2H), 2.66 (d, J=5.8 Hz, 1H), 1.88 (d, J=5.8 Hz, 1H), 1.36 (s, 3H), 1.30 (t, J=7.2 Hz, 3H), 0.92 (s, 3H).

Example 18c trans-3-(2,2-difluoro-benzo[1,3]-dioxol-5-yl)-2,2-dimethylcyclopropanecarboxylic acid

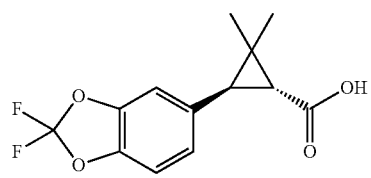 [SMILES: CCOC(=O)[C@@H]1[C@@H](c2ccc3c(c2)OC(F)(F)O3)C1(C)C]

Ethyl trans-3-(2,2-difluoro-benzo[1,3]dioxol-5-yl)-2,2-dimethylcyclopropanecarboxylate (1.62 g, 5.4 mmol) was reacted as described under General Procedure C to furnish the title compound (1.37 g, 93%) as a white solid. $^1$H NMR (300 MHz, CDCl$_3$) δ 6.97 (d, J=7.5 Hz, 1H), 6.89 (s, 1H), 6.87 (d, J=7.5 Hz, 1H), 2.72 (d, J=5.8 Hz, 1H), 1.90 (d, J=5.8 Hz, 1H), 1.42 (s, 3H), 0.96 (s, 3H).

Example 18d trans-N-(5-Chloro-2-methoxyphenyl)-3-(2,2-difluoro-benzo[1,3]dioxol-5-yl)-2,2-dimethyl-cyclopropane carboxamide

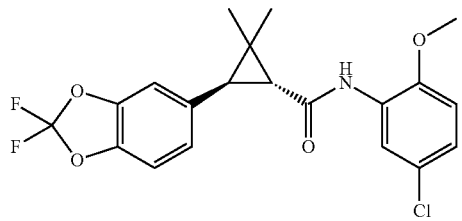 [SMILES: COc1ccc(Cl)cc1NC(=O)[C@@H]1[C@@H](c2ccc3c(c2)OC(F)(F)O3)C1(C)C]

trans-3-(2,2-difluoro-benzo[1,3]dioxol-5-yl)-2,2-dimethyl-cyclopropanecarboxylic acid (450 mg, 1.7 mmol) and 4-chloro-2-methoxyaniline (318 mg, 2.0 mmol) were reacted as described under General Procedure D to furnish the title compound (80 mg, 12%) as a white solid. $^1$H NMR (300 MHz, CDCl$_3$) δ 8.49 (s, 1H), 7.98 (s, 1H), 7.02-6.90 (m, 4H), 6.80 (d, J=8.7 Hz, 1H), 3.92 (s, 3H), 2.82 (d, J=5.5 Hz, 1H), 1.81 (d, J=5.5 Hz, 1H), 1.39 (s, 3H), 0.98 (s, 3H). mp 120-122° C. ESIMS m/z [M+H]$^+$ 410.3.

Pharmacology

Example 1

CellLux Fluorescence Assay to Detect Agonists and Positive Allosteric Modulators of α7 nAChR Compounds were screened for positive allosteric modulation (PAM) of α7nACh receptors on the CellLux (Perkin Elmer) with a fluorescence-based calcium assay. Activation of the α7nAChR by endogenous ligands, results in a calcium flux which can be measured using ion specific fluorescent dyes. The fluorescence assay was run in a high throughput format on the CellLux, an automated fluorescent plate reader with liquid handling capabilities. The assay measured intracellular calcium changes in a GH4C1 cell line stably expressing α7nACh receptors, when treated with compounds that positively modulated an ACh-induced response. Compound was added first to identify any agonist activity followed by ACh addition (EC20 concentration) to measure PAM activity.

Prior to assay, α7/GH4C1 cells were seeded in 96-well plates (PDL-coated) and incubated for 48 hours at 33° C. in 5% $CO_2$. The cells were grown in F10Ham media plus 15% horse serum, 2.5% FCS, 2 mM penicillin, 2 mM streptomycin, 2 mM glutamine and 10 mM Hepes (Invitrogen). 0.5 mM sodium butyrate, a growth arrestor, was added to the cells during the incubation period to increase expression of α nAChR. On the day of assessment, the media was removed and the cells were washed with HBSS buffer (1 mM $CaCl_2$, 0.5 mM $MgCl_2$, 0.4 mM $MgSO_4$, 5 mM KCL, 0.4 mM $KHPO_4$, 4 mM $NaHCO_3$, 137 mM NaCl, 0.3 mM $Na_2HPO_4$, 5.5 mM glucose and 1M Hepes, pH7.4) and then Fluo-4 Direct Calcium dye (Molecular Probes) was added. The cells were incubated with dye for 30 minutes at 33° C. Compound addition, ACh addition and fluorescence measurement was performed on the CellLux, a high throughput imaging system. Fluorescent excitation is at 495 nm and emission at 516 nm.

The CellLux recorded fluorescent responses at 5 second intervals starting with a 10 second baseline reading, the compound was then added and the response was read for 1 minute. ACh was then added and the response read for a further 2 minutes, a total of 4 minutes. This protocol detects agonist and PAM activity of compounds at the α7nAChR.

Compounds were tested at 6 doses, in triplicate, 0.03, 0.1, 0.3, 1, 3 and 10 uM. Working stocks were prepared in DMSO from 10 mM DMSO stocks and then 10× starting stocks were prepared by diluting 1:100 in HBSS buffer (0.1% DMSO final). A 10× starting dilution of an EC20 concentration of ACh was prepared in HBSS buffer (0.1% DMSO final). Negative control was HBSS buffer (0.1% DMSO final).

Data was analysed by calculating % potentiation of compound compared to the ACh control response, where ACh potentiation was set at 0%. Peak/base values were calculated for each compound concentration (n=3) using AssayPro program (CellLux) and these values were used to determine % potentiation based on the ACh control peak/base value. Compounds were identified as active if they showed potentiation over the control ACh response. For active compounds % potentiation values were analysed to determine compound EC50 values using GraphPad Prism 4.

Example 2

Electrophysiology for α7 nAChR Positive Allosteric Modulator Activity

Compounds were screened for positive allosteric modulation (PAM) of α7 nACh receptors using the whole-cell patch clamp technique. The α7nAChR activates and desensitizes very rapidly. Rapid ligand application and response recording is crucial. The current was measured in a GH4C1 cell line stably expressing α7nAChR, when treated with compounds that positively modulated an ACh-induced response. Compound was added first to identify any agonist activity followed by Ach addition (EC20 concentration) to measure PAM activity.

α7/GH4C1 cells were seeded in T75 flasks and incubated for 48 hours at 33° C. in 5% $CO_2$, prior to patch-clamp recording. The cells were grown in F10Ham media plus 15% horse serum, 2.5% FCS, 2 mM penicillin, 2 mM streptomycin, 2 mM glutamine and 10 mM Hepes (Invitrogen). 0.5 mM sodium butyrate, a growth arrestor, was also added to the cells during the incubation period to increase α7 nAChR expression. On the day of assay the media was removed, the cells were centrifuged and re-suspended in bath solution (160 mM NaCl, 4.5 mM KCl, 2 mM $CaCl_2$, 1 mM $MgCl_2$, 5 mM glucose and 10 mM Hepes, pH7.4).

Whole-cell nAChR currents were recorded in α7/GH4C1 cells clamped at −60 mV using a planar electrode patch clamp system (Port-A-Patch, Nanion) interfaced to an EPC10 patch clamp amplifier (Heka electronic) Cells were continuously bathed in a solution containing (mM): 160 NaCl, 4.5 KCl, 7.66 $CaCl_2$, 1 $MgCl_2$, 5 glucose and 10 Hepes, pH7.4, NaOH, 310-320 mOsmol·$Kg^{-1}$). ACh was rapidly applied for 1 sec using a gravity feed perfusion system (Nanion Technologies) under direct digital control of the EPC 10 amplifier. Other drugs were perfused directly into the bath. Cells were washed for 2-3 minutes in between ACh applications to allow adequate recovery from desensitization. PAM activity was measured by applying compound with and without ACh (EC20 concentration).

Compounds were tested at 6 doses, 0.03, 0.1, 0.3, 1, 3 and 10 uM on 2-3 cells. Working stocks were prepared in DMSO from 10 mM DMSO stocks and then final stocks were prepared by diluting 1:200 in external bath solution (0.5% DMSO final). An EC20 concentration of ACh was prepared in external bath solution.

Peak current and area under the curve were measured using Fitmaster (HEKA) software. PAM activity was measured by % potentiation which was calculated from peak current or area under the curve values based on the ACh control response. Concentration-response curves and $EC_{50}$ values were analysed using GraphPad Prism 4.

Example 3

Animal Model of Cognitive Enhancement—T-maze Continuous Alternation Task (T-CAT)

The cognition enhancing properties of the compounds in the invention were evaluated in an animal model where cognitive impairment is pharmacologically induced. Scopolamine is a muscarinic receptor antagonist which is used as a standard/reference drug for inducing cognitive deficits in healthy humans and animals.

The T-maze Continuous Alternation Task (T-CAT) measures spontaneous alternation, which is the innate tendency of mice to alternate free choices in a T-maze over a series of successive runs. This sequential procedure relies on working memory and is sensitive to various pharmacological manipulations affecting memory processes.

The T-maze apparatus is made of gray Plexiglas with a main stem (55 cm long×10 cm wide×25 cm high) and two arms (30 cm long×10 cm wide×25 cm high) positioned at 90 degree angle relative to the main stem. A start box (15 cm long×10 cm wide) is separated from the main stem by a sliding door. Sliding doors are also provided to close specific arms during the forced-choice alternation task.

The experimental protocol consists of one single session, which starts with 1 "forced-choice" trial, followed by 14 "free-choice" trials. In the first "forced-choice" trial, the animal is confined for 5 s in the start arm and then it is released while either the left or right goal arm is blocked by a sliding door. The animal will negotiate the maze, eventually enter the open goal arm, and return to the start position. Immediately after the return to the start position, the left or right goal door is opened and the animal is allowed to choose freely between the left and right goal arm ("free choice" trials). The animal is considered to have entered an arm when it places its four paws in the arm. A session is terminated and the animal is removed from the maze as soon as 14 free-choice trials have been performed or 10 min have elapsed, whichever event occurs first. The percentage of alternation over the 14 free-choice trials is determined for each mouse and is used as an index of working memory performance. This percentage is defined as entry in a different arm of the T-maze over successive visits (i.e., left-right-left-right, etc). Scopolamine administered 20 min prior the initiation of the 1-maze session is used to induce disruption in the spontaneous alternation of mice. Test compounds are administered 60 min prior the start of the T-maze session in order to evaluate their ability to reverse the scopolamine effect.

The apparatus is cleaned between each animal using alcohol (70°). Urine and feces are removed from the maze. During the trials, animal handling and the visibility of the operator are minimized as much as possible.

The supporting compounds listed below were screened in the fluorescence-based calcium assay and gave significant potentiation of ACh at compound concentrations <10 uM: 1b, 2b, 3b, 4b, 6b, 7b, 8b, 11b, 12c, 13b, 14c, 15b, 16e, 17b, 18d.

The supporting compounds listed below were screened in the T-CAT model and showed significant improvement relative to the scopolamine treated mice: 2b, 4b, 5a, 6b, 9b, 10b.

What we claim is:

1. A compound of formula (I) or a salt thereof:

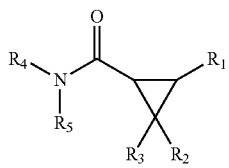

(I)

wherein
R$_1$ is selected from optionally substituted aryl, optionally substituted heteroaryl (excluding optionally substituted porphyrins), or optionally substituted heterocyclyl;
R$_2$ is selected from C$_1$-C$_4$ alkyl, C$_3$-C$_5$ alkenyl, F, Br, Cl, CN, or C$_1$-C$_4$ haloalkyl;
R$_3$ is selected from hydrogen, C$_1$-C$_4$ alkyl, C$_3$-C$_5$ alkenyl, F, Br, Cl, CN, or C$_1$-C$_4$ haloalkyl; or
R$_2$ and R$_3$ together form C$_{4-9}$ cycloalkyl or C$_{4-9}$ cycloalkenyl;
R$_4$ is selected from optionally substituted heteroaryl, optionally substituted heterocyclyl, or optionally substituted aryl;
R$_5$ is selected from hydrogen or optionally substituted alkyl;
wherein when both R$_2$ and R$_3$ are Cl, R$_4$ is an optionally substituted heteroaryl or optionally substituted heterocyclyl, and provided that the following compounds are excluded:

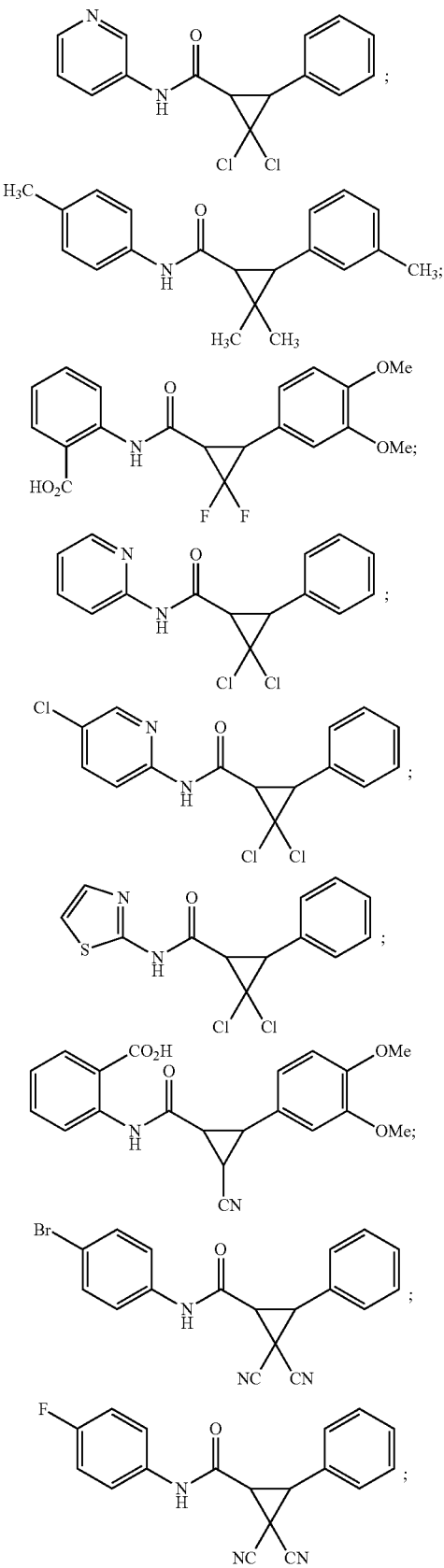

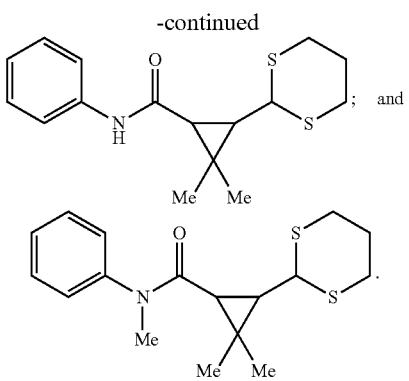

and

2. A compound of formula (II) or a salt thereof:

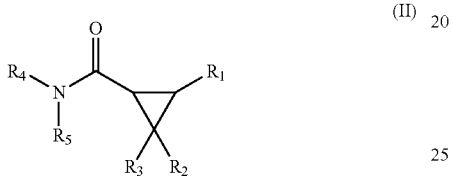

wherein
  $R_1$ is selected from optionally substituted aryl, optionally substituted heteroaryl or optionally substituted heterocyclyl;
  $R_2$ and $R_3$ together form $C_{4-9}$ cycloalkyl;
  $R_4$ is selected from optionally substituted heteroaryl, optionally substituted heterocyclyl, or optionally substituted aryl; and
  $R_5$ is selected from hydrogen or optionally substituted alkyl.

3. A compound according to claim 1, represented by formula (Ia), or a salt thereof:

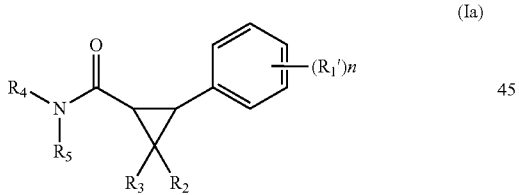

wherein
  each $R_1'$ is independently selected from the group consisting of cyano, halo, nitro, optionally substituted lower alkyl, optionally substituted aryl, optionally substituted aryloxy, optionally substituted arylalkyl, optionally substituted heteroaryl, optionally substituted heterocyclyl, optionally substituted $C_{3-7}$ cycloalkyl, —OR, —C(O)R, —C(O)OR, —OC(O)R (where R is selected from hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl), —C(O)NR'R", —NR'C(O)R", —S(O)$_2$—NR'R" and —NR'R" (where R' and R" are independently selected from hydrogen or lower alkyl), —S(O)R''' (where R''' is lower alkyl, or cycloalkyl), —S(O)$_2$R''' (where R''' is lower alkyl, cycloalkyl or OH), or any two adjacent $R_1'$ together form heterocyclyl or heteroaryl;

n is 0 or an integer from 1 to 5;

$R_2$ is selected from $C_1$-$C_4$ alkyl, $C_3$-$C_5$ alkenyl, F, Br, Cl, CN, or $C_1$-$C_4$ haloalkyl;

$R_3$ is selected from hydrogen, $C_1$-$C_4$ alkyl, $C_3$-$C_5$ alkenyl, F, Br, Cl, CN, or $C_1$-$C_4$ haloalkyl; or $R_2$ and $R_3$ together form $C_{4-9}$ cycloalkyl or $C_{4-9}$ cycloalkenyl;

$R_4$ is selected from optionally substituted heteroaryl, optionally substituted heterocyclyl, or optionally substituted aryl;

$R_5$ is selected from hydrogen or optionally substituted alkyl;

wherein when both $R_2$ and $R_3$ are Cl, $R_4$ is an optionally substituted heteroaryl or optionally substituted heterocyclyl, and provided that the following compounds are excluded:

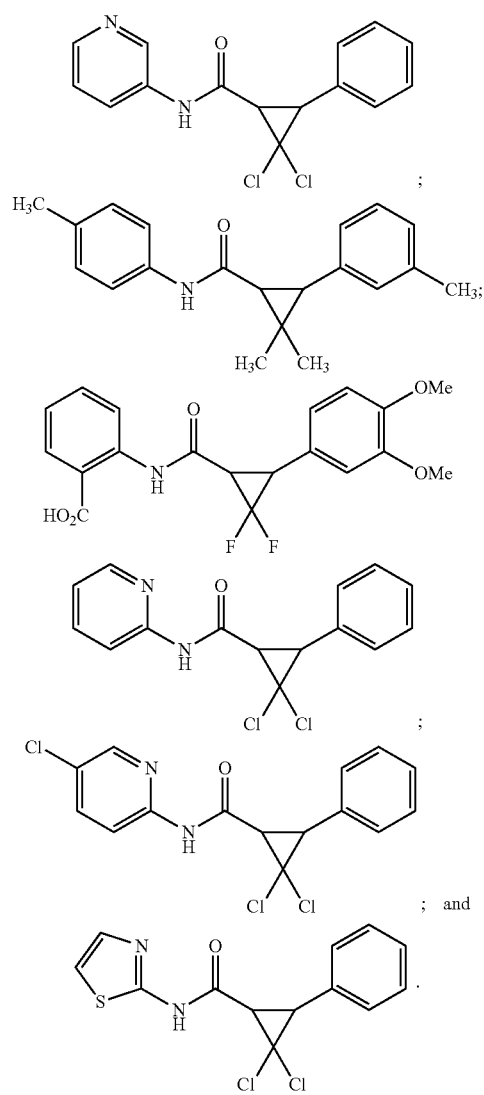

4. A compound according to claim 1, represented by formula (Ib), or a salt thereof:

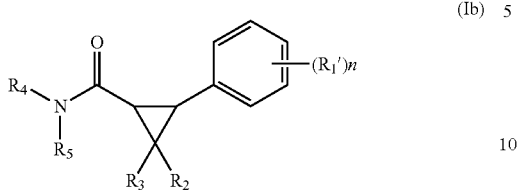

wherein
each $R_1'$ is independently selected from the group consisting of cyano, halo, nitro, optionally substituted lower alkyl, optionally substituted aryl, optionally substituted aryloxy, optionally substituted arylalkyl, optionally substituted heteroaryl, optionally substituted heterocyclyl, optionally substituted $C_{3-7}$ cycloalkyl, —OR, —C(O)R, —C(O)OR, —OC(O)R (where R is selected from hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl), —C(O)NR'R", —NR'C(O)R", —S(O)$_2$—NR'R" and —NR'R" (where R' and R" are independently selected from hydrogen or lower alkyl), —S(O)R''' (where R''' is lower alkyl, or cycloalkyl), —S(O)$_2$R''' (where R''' is lower alkyl, cycloalkyl or OH), or any two adjacent $R_1'$ together form heterocyclyl or heteroaryl;
n is 0 or an integer from 1 to 5;
$R_2$ is selected from $C_1$-$C_4$ alkyl, $C_3$-$C_5$ alkenyl, $C_1$-$C_4$ haloalkyl, F, Cl or Br;
$R_3$ is selected from hydrogen, $C_1$-$C_4$ alkyl, $C_3$-$C_5$ alkenyl, $C_1$-$C_4$ haloalkyl, or Br; or
$R_2$ and $R_3$ together form $C_{4-9}$ cycloalkyl or $C_{4-9}$ cycloalkenyl;
$R_4$ is selected from optionally substituted heteroaryl, optionally substituted heterocyclyl, or optionally substituted aryl;
$R_5$ is independently selected from hydrogen, or optionally substituted alkyl;
provided that the following compound is excluded:

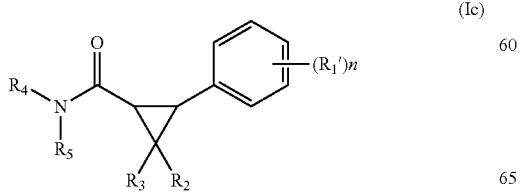

5. A compound according to claim 1, represented by formula (Ic), or a salt thereof:

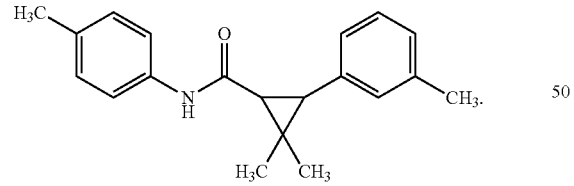

wherein
each $R_1'$ is independently selected from the group consisting of cyano, halo, nitro, optionally substituted lower alkyl, optionally substituted aryl, optionally substituted aryloxy, optionally substituted arylalkyl, optionally substituted heteroaryl, optionally substituted heterocyclyl, optionally substituted $C_{3-7}$ cycloalkyl, —OR, —C(O)R, —C(O)OR, —OC(O)R (where R is selected from hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl), —C(O)NR'R", —NR'C(O)R", —S(O)$_2$—NR'R" and —NR'R" (where R' and R" are independently selected from hydrogen or lower alkyl), —S(O)R''' (where R''' is lower alkyl, or cycloalkyl), —S(O)$_2$R''' (where R''' is lower alkyl, cycloalkyl or OH), or any two adjacent $R_1'$ together form heterocyclyl or heteroaryl;
n is 0 or an integer from 1 to 5;
$R_2$ is selected from $C_1$-$C_4$ alkyl, $C_3$-$C_5$ alkenyl, $C_1$-$C_4$ haloalkyl, F, Cl or Br;
$R_3$ is selected from hydrogen, $C_1$-$C_4$ alkyl, $C_3$-$C_5$ alkenyl, $C_1$-$C_4$ haloalkyl, or Br; or
$R_2$ and $R_3$ together form $C_{4-9}$ cycloalkyl or $C_{4-9}$ cycloalkenyl;
$R_4$ is selected from heteroaryl which may be independently substituted by one to three substituents selected from halogen, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, —OH, phenyl, benzyl, phenoxy, benzyloxy, benzoyl, —NH$_2$, —NHC$_{1-4}$ alkyl, —N(C$_{1-4}$ alkyl)$_2$, —CN, —NO$_2$, mercapto, —S(O)$_2$NH$_2$, —S(O)$_2$NHC$_{1-4}$ alkyl, —S(O)$_2$N(C$_{1-4}$ alkyl)$_2$, $C_{1-6}$ alkylcarbonyl, $C_{1-6}$ alkoxycarbonyl, CO$_2$H, —S(O)R''' (where R''' is lower alkyl or cycloalkyl) and —S(O)$_2$R''' (where R''' is lower alkyl, cycloalkyl or OH); or aryl which may be independently substituted by one to three substituents selected from halogen, $C_{2-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, —OH, phenyl, benzyl, phenoxy, benzyloxy, benzoyl, —NH$_2$, —NHC$_{1-4}$ alkyl, —N(C$_{1-4}$ alkyl)$_2$, —CN, —NO$_2$, mercapto, —S(O)$_2$NH$_2$, —S(O)$_2$NHC$_{1-4}$ alkyl, —S(O)$_2$N(C$_{1-4}$ alkyl)$_2$, $C_{1-6}$ alkylcarbonyl, $C_{1-6}$ alkoxycarbonyl, CO$_2$H, —S(O)R''' (where R''' is lower alkyl or cycloalkyl) and —S(O)$_2$R''' (where R''' is lower alkyl, cycloalkyl or OH); and
$R_5$ is independently selected from hydrogen, or lower alkyl.

6. A compound according to claim 1, represented by formula (IIa), or a salt thereof:

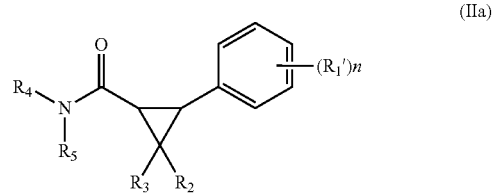

wherein
each $R_1'$ is independently selected from the group consisting of cyano, halo, nitro, optionally substituted lower alkyl, optionally substituted aryl, optionally substituted aryloxy, optionally substituted arylalkyl, optionally substituted heteroaryl, optionally substituted heterocyclyl, optionally substituted $C_{3-7}$ cycloalkyl, —OR, —C(O)R, —C(O)OR, —OC(O)R (where R is selected from hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl), —C(O)NR'R", —NR'C(O)R", —S(O)$_2$—NR'R" and —NR'R" (where R' and R" are independently selected from hydrogen or lower alkyl), —S(O)R''' (where R''' is lower alkyl, or cycloalkyl), —S(O)$_2$R''' (where R''' is lower alkyl, cycloalkyl or OH), or any two adjacent $R_1$' together form heterocyclyl or heteroaryl;

n is 0 an integer from 1 to 5;

$R_2$ and $R_3$ together form $C_{4-9}$ cycloalkyl;

$R_4$ is selected from optionally substituted heteroaryl, optionally substituted heterocyclyl, or optionally substituted aryl; and $R_5$ is independently selected from hydrogen or optionally substituted alkyl.

7. A compound according to claim 1 or salt thereof, wherein $R_1$ is an optionally substituted aryl or optionally substituted heteroaryl group.

8. A compound according to claim 2, or salt thereof, wherein $R_1$ is an optionally substituted aryl or optionally substituted heteroaryl group.

9. A compound according to claim 1, or salt thereof, wherein $R_4$ is selected from heteroaryl or aryl each of which may be independently substituted by one to three substituents selected from halogen, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, —OH, phenyl, benzyl, phenoxy, benzyloxy, benzoyl, —NH$_2$, —NHC$_{1-4}$ alkyl, —N(C$_{1-4}$ alkyl)$_2$, —CN, —NO$_2$, mercapto, —S(O)$_2$NH$_2$, —S(O)$_2$NHC$_{1-4}$ alkyl, —S(O)$_2$N(C$_{1-4}$ alkyl)$_2$, $C_{1-6}$ alkylcarbonyl, $C_{1-6}$ alkoxycarbonyl, CO$_2$H, —S(O)R''' (where R''' is lower alkyl or cycloalkyl) and —S(O)$_2$R''' (where R''' is lower alkyl, cycloalkyl or OH).

10. A compound according to claim 1, or salt thereof, where $R_4$ is selected from:

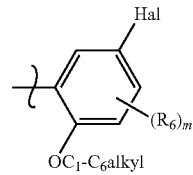

(a)

wherein

Hal is a halogen;

m is 0, 1 or 2; and each $R_6$ is independently selected from halogen, hydroxy, CN, NO$_2$, haloalkyl, aryl, heteroaryl, $C_{1-3}$ alkoxy, $C_{1-3}$ alkyl, or CO$_2$R' (where R' is a lower alkyl or H);

or (b) a heteroaryl substituted from 1 to 3 times from a group selected from $C_1$-$C_3$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, —OH, phenyl, benzyl, phenoxy, benzyloxy, benzoyl, —NH$_2$, —NHC$_{1-4}$ alkyl, —N(C$_{1-4}$ alkyl)$_2$, —CN, —NO$_2$, mercapto, $C_{1-6}$ alkylcarbonyl, $C_{1-6}$ alkoxycarbonyl, CO$_2$H, —S(O)R''' (where R''' is lower alkyl or cycloalkyl) and —S(O)$_2$R''' (where R''' is lower alkyl, cycloalkyl or OH).

11. A compound according to claim 10, or a salt thereof, wherein the heteroaryl is pyridinyl, pyrazolyl or thiazolyl.

12. A compound according to claim 1, or a salt thereof, wherein $R_2$ and $R_3$ are $C_1$-$C_4$ alkyl.

13. A compound according to claim 1, or a salt thereof, wherein $R_2$ and $R_3$ are methyl or ethyl.

14. A compound according to claim 1, or a salt thereof, wherein $R_5$ is hydrogen or $C_{1-3}$ alkyl.

15. A compound according to claim 3, or a salt thereof, wherein n is 0, 1, 2, or 3, and $R_1$', when present, is halogen, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, —OH, phenyl, benzyl, phenoxy, benzyloxy, benzoyl, —NH$_2$, —NHC$_{1-4}$ alkyl, —N(C$_{1-4}$ alkyl)$_2$, —CN, —NO$_2$, mercapto, —S(O)$_2$NH$_2$, —S(O)$_2$NHC$_{1-4}$ alkyl, —S(O)$_2$N(C$_{1-4}$ alkyl)$_2$, $C_{1-6}$ alkylcarbonyl, $C_{1-6}$ alkoxycarbonyl, CO$_2$H, —S(O)R''' (where R''' is lower alkyl or cycloalkyl) and —S(O)$_2$R''' (where R''' is lower alkyl, cycloalkyl or OH).

16. A method for the treatment of cognitive deficits associated with neurodegeneration or neuropsychiatric diseases, said method including the step of administering a compound according to claim 1, or a pharmaceutically acceptable salt thereof, or a composition comprising a compound according to claim 1, or a pharmaceutically acceptable salt thereof.

17. A method for the treatment of inflammatory diseases, said method including the step of administering a compound according to claim 1, or a pharmaceutically acceptable salt thereof, or a composition comprising a compound according to claim 1, or a pharmaceutically acceptable salt thereof.

18. A method of positively modulating α7nAChRs in a cell by contacting the cell with a compound according to claim 1, or a salt thereof, to said cell.

* * * * *